United States Patent
Xu et al.

(10) Patent No.: US 10,813,849 B2
(45) Date of Patent: *Oct. 27, 2020

(54) RECHARGEABLE CALCIUM PHOSPHATE-CONTAINING DENTAL MATERIALS

(71) Applicant: University of Maryland, Baltimore, Baltimore, MD (US)

(72) Inventors: Huakun Xu, Frederick, MD (US); Michael D. Weir, Silver Spring, MD (US); Ling Zhang, Shaanxi (CN)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/017,123

(22) Filed: Feb. 5, 2016

(65) Prior Publication Data

US 2016/0228335 A1     Aug. 11, 2016

Related U.S. Application Data

(60) Provisional application No. 62/112,438, filed on Feb. 5, 2015.

(51) Int. Cl.

| | |
|---|---|
| *A61K 6/00* | (2020.01) |
| *A61K 31/14* | (2006.01) |
| *A61K 33/42* | (2006.01) |
| *A61Q 11/00* | (2006.01) |
| *A61P 31/04* | (2006.01) |
| *A61K 6/838* | (2020.01) |
| *A61K 6/17* | (2020.01) |
| *A61K 6/62* | (2020.01) |
| *A61K 6/71* | (2020.01) |
| *A61K 6/77* | (2020.01) |
| *A61K 6/802* | (2020.01) |
| *A61K 6/887* | (2020.01) |

(52) U.S. Cl.
CPC ............ *A61K 6/838* (2020.01); *A61K 6/17* (2020.01); *A61K 6/62* (2020.01); *A61K 6/71* (2020.01); *A61K 6/77* (2020.01); *A61K 6/802* (2020.01); *A61K 6/887* (2020.01)

(58) Field of Classification Search
CPC ... A61K 6/30; A61K 6/17; A61K 6/54; A61K 6/35; A61K 6/887; A61K 6/71; A61K 6/77; A61K 6/838; A61K 6/889; A61K 2800/413; A61K 31/14; A61Q 11/00; A61P 31/04

See application file for complete search history.

(56) References Cited

U.S. PATENT DOCUMENTS

| | | | | |
|---|---|---|---|---|
| 4,177,258 A | * | 12/1979 | Gaffar | A61K 8/21 424/49 |
| 6,413,498 B1 | * | 7/2002 | Malmagro | A61K 6/033 424/49 |
| 2005/0154081 A1 | * | 7/2005 | Yin | A61K 6/083 523/115 |
| 2006/0270752 A1 | * | 11/2006 | Xu | A61L 27/44 523/116 |
| 2008/0300340 A1 | * | 12/2008 | Gross | A61K 6/083 523/120 |
| 2010/0129777 A1 | * | 5/2010 | Ziegler | A61K 6/0023 433/215 |
| 2013/0108708 A1 | * | 5/2013 | Xu | A61K 6/0008 424/618 |

FOREIGN PATENT DOCUMENTS

| | | | | | |
|---|---|---|---|---|---|
| WO | WO 9414406 A1 | * | 7/1994 | | A61K 8/24 |
| WO | WO-0025697 A1 | * | 5/2000 | | A61K 8/347 |
| WO | WO 2007066837 A1 | * | 6/2007 | | A61K 8/733 |
| WO | WO 2013119901 A1 | * | 8/2013 | | A61K 6/0067 |

OTHER PUBLICATIONS

Moszner et al. New Polymer-Chemical Developments in Clinical Dental Polymer Materials: Enamel-Dentin Adhesives and Restorative Composites. Aug. 6, 2012. Journal of Polymer Science. vol. 50. pp. 4369-4402. (Year: 2012).*

* cited by examiner

*Primary Examiner* — Tracy Liu

(74) *Attorney, Agent, or Firm* — Wenderoth, Lind & Ponack, L.L.P.

(57) ABSTRACT

The present invention provides rechargeable dental materials that can be widely applied in a variety of dental applications. The rechargeable dental materials of the invention may be included in dental primers, dental adhesives, dental resins, dental composites, dental bonding systems and the like, as well as dental cements, dental sealants, dental bases and dental liners, each of which is rechargeable with calcium and phosphate ions. The present invention also provides for a method of recharging the rechargeable dental material with calcium and phosphate ions.

13 Claims, 14 Drawing Sheets

RECHARGEABLE CALCIUM PHOSPHATE-CONTAINING DENTAL MATERIALS

STATEMENT REGARDING FEDERALLY SPONSORED RESEARCH

This invention was made with government support under Grant Number DE017974 awarded by the National Institutes of Health. The government has certain rights in the invention.

BACKGROUND

Failure of tooth cavity restorations cost dental patients in the United States more than $46 billion annually [1]. Development of secondary caries at the tooth-restoration interface is a primary reason for restoration failure [2-4], and replacing the failed restorations accounts for 50% to 70% of all restorations performed [5-6]. There is a great need to inhibit caries and increase the longevity of the restorations.

Calcium phosphate dental resins and composites used in restorations can release calcium and phosphate ions to inhibit caries, remineralize tooth lesions, and regenerate the lost minerals in tooth structures. However, the release of these ions lasts for only a few months, after which the release diminishes and gradually stops. Tooth restorations are intended to serve orally for much longer than a few months. Therefore, it would be highly desirable to have dental resins and composites that exhibit sustained long-term release of calcium and phosphate ions to inhibit caries and remineralize tooth lesions. The present invention is directed to the development of such dental resins and composites, and other important goals.

SUMMARY

The tooth-resin bond is the weak link in dental restorations as development of secondary caries at the margins of such bonds remains a primary reason for restoration failure. Calcium phosphate-containing resins are promising tools as they release calcium (Ca) and phosphate (P) ions which inhibit formation of caries and promote remineralization. However, the release of Ca and P ions from such resins is short-term, with ion release dissipating after only a couple of months. Through diligent efforts, the present inventors have developed new dental materials that address this shortcoming. As reported herein, dental materials in which the Ca and P ion content can be recharged have been developed. Such rechargeable dental materials provide the means for long-term Ca and P ion release that can provide for continuous remineralization and inhibition of caries in dental applications. The rechargeable dental materials described herein, and the corresponding methods for recharging such materials that are also disclosed, are applicable to such dental products as dental resins, adhesives, composites and cements, and can be used to combat caries and remineralize tooth lesions.

Briefly, disclosed herein are rechargeable calcium phosphate-based dental materials that can be widely applied to a variety of dental products and applications. The rechargeable calcium phosphate-based dental materials of the invention may be included in dental primers, dental resins, dental bases, dental liners, tooth carie restorations, dental composites (such as flowable composites, low-shrinkage composites, and non-shrinking composites), bonding agents, adhesives, sealants (such as pit and fissure sealants), varnish, cements (such as orthodontic cements, crown cements, and inlay/onlay cements), coatings (such as tooth coatings and root surface coatings), and other dental products containing a resin component. Specific embodiments and aspects of the invention are summarized in the following paragraphs.

In a first embodiment, the invention is directed to a rechargeable dental material comprising (i) one or more rechargeable monomers and (ii) nanoparticles of amorphous calcium phosphate (NACP), wherein the combined amount of the one or more rechargeable monomers is about 10% to about 90% of the mass of the material, and wherein the NACP is present in an amount of about 20% to about 40% of the mass of the material.

In a second embodiment, the invention is directed to a rechargeable dental adhesive that comprises a rechargeable dental material as defined herein and one or more curing agents, wherein the combined amount of the one or more curing agents is about 0.05% to about 5% of the mass of the adhesive, and wherein the NACP is present in an amount of about 20% to about 30% by mass of the rechargeable dental material used in the adhesive.

In a third embodiment, the invention is directed to a rechargeable dental cement that comprises a rechargeable dental material as defined herein and one or more curing agents, wherein the combined amount of the one or more curing agents is about 0.05% to about 5% of the mass of the cement, and wherein the NACP is present in an amount of about 30% to about 40% by mass of the rechargeable dental material used in the cement.

In a fourth embodiment, the invention is directed to a rechargeable dental composite that comprises a rechargeable dental material as defined herein and one or more fillers, wherein the combined amount of the one or more fillers is about 30% to about 70% of the mass of the composite. In certain aspects, the filler is one or more of a glass filler, a ceramic filler, and a polymer-based filler.

In each aspect and embodiment of the invention, the rechargeable monomers include, but are not limited to, bisphenol glycidyl methacrylate (bis-GMA), triethylene glycol dimethacrylate (TEGDMA), 2-hydroxyethyl methacrylate (HEMA), urethane dimethacrylate (UDMA), pyromellitic acid glycerol dimethacrylate (PMGDM), ethoxylated bisphenol A dimethacrylate (EBPADMA), Bis[2-(methacryloyloxy)ethyl] phosphate (BisMEP), methacryloyloxyethyl phthalate (MEP), methacrylate-modified polyalkenoic acid, pyromellitic dimethacrylate (PMDM), glycerol dimethacrylate/maleate adduct, glycerol dimethacrylate/succinate adduct, 2-acetoacetoxyethyl methacrylate, and methacryloyloxyethyl maleate.

As indicated above, the rechargeable dental materials and the rechargeable dental adhesives, rechargeable dental cements and rechargeable dental composites comprising the rechargeable dental materials in the noted embodiments of the invention, comprise at least one rechargeable monomer. In certain aspects of each of these embodiments, the rechargeable dental materials may comprise two or more, three or more, or four or more rechargeable monomers, or one, two, three, four, or more of the rechargeable monomers.

In certain aspects of the dental materials of the four embodiments, the NACP has an average particle size of about 10 nm to about 500 nm.

The dental materials of the four embodiments of the invention may, in certain aspects, also comprise one or more of acidic methacrylate or acrylate-based monomers.

The dental materials of the four embodiments may, in certain aspects, also comprise one or more antibacterial agents. Acceptable antibacterial agents include, but not limited to, antibacterial monomers, quaternary ammonium salts (QASs), silver-containing nanoparticles (NanoAgs), chlorhexidine particles, TiO2 particles, and ZnO particles.

When antibacterial monomers are included in the dental materials, the antibacterial monomers include, but are not limited to, dimethylamino propyl methacrylate (DMAPM), dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMAUDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), and dimethylamino docosyl methacrylate (DMADOM).

The dental materials of the four embodiments may, in certain aspects, also comprise one or more protein repellant materials. Acceptable protein repellant materials include, but are not limited to, 2-methacryloyloxyethyl phosphorylcholine (MPC), poly(hydroxyethyl methacrylate) (HEMA) and derivatives thereof, and poly(N-isopropylacrylamide) and derivatives thereof.

The dental materials of the four embodiments may, in certain aspects, also comprise one or more curing agents. Acceptable curing agents include, but are not limited to, photo-curing agents, such as camphorquinone (CQ), ethyl 4-N,N-dimethylaminobenzoate and phenylbis (2,4,6-triemthylbenzoyl) phosphine oxide, and chemical curing agents, such as benzoyl peroxide (BPO).

In certain aspects of the fourth embodiment, the glass filler is one or more types of glass particles that include, but are not limited to, barium boroaluminosilicate glass particles, fluoroaluminosilicate glass particle modified with a polyalkenoic acid, and fluoroaluminosilicate glass particles modified with a polycarboxylic acid.

In certain aspects of the fourth embodiment, the rechargeable dental composite comprises (i) a rechargeable dental material, wherein the rechargeable monomers are present in a combined amount of 10% to about 40% by mass of the material and the NACP is present in amount of about 20% to about 30% by mass of the material, and (ii) a filler, wherein the filler is present in an amount of about 40% to about 60% by mass of the composite.

Also described herein are methods of recharging the rechargeable dental materials of the invention, and the rechargeable dental adhesives, rechargeable dental cements and rechargeable dental composites comprising the rechargeable dental materials defined in the noted embodiments, with calcium ions, phosphate ions or combinations thereof. That is, the rechargeable dental materials are capable of being recharged with calcium ions, phosphate ions, or both. After the rechargeable dental material has been applied to the tooth of a subject in whichever form is applicable, the rechargeable dental materials provide calcium and phosphate ions to the tooth to which it was applied and surrounding teeth. As the rechargeable dental material can be recharged with calcium ions and phosphate ions, they can continue to release ions over the life span of the dental material.

Thus, and in a fifth embodiment, the invention is directed to methods of recharging a rechargeable dental material comprising contacting a rechargeable dental material of the present invention (or a rechargeable dental adhesive, rechargeable dental cement, or rechargeable dental composite comprising a rechargeable dental material of the present invention) with a recharging composition under conditions promoting uptake of ions by the rechargeable monomers.

Acceptable recharging compositions include, but are not limited to, tooth pastes, mouthwashes, oral gels, gums, dental pastes, and oral patches, each of which comprises calcium and/or phosphate ions.

In certain aspects of this embodiment, the recharging composition is in contact with the rechargeable dental material for about 30 seconds to about 3 minutes.

In certain aspects of this embodiment, the rechargeable dental material is contacted with the recharging composition daily, weekly, or monthly.

The invention also includes kits comprising the rechargeable dental material of the present invention, or a rechargeable dental adhesive, rechargeable dental cement, or rechargeable dental composite comprising a rechargeable dental material of the present invention, and written directions for use. When the kit comprises a rechargeable dental adhesive or a rechargeable dental cement, the kit may further include a primer and/or an etchant.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment or aspect disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE DRAWINGS

(FIG. 2A) Flexural strength and (FIG. 2B) elastic modulus of the three NACP nanocomposites and the two resin-modified glass ionomer (RMGI) controls. Each value is mean±sd (n=6). NACP nanocomposites had strengths approximately 3-4 fold of, and elastic moduli generally similar to, those of RMGIs. In each plot, values with dissimilar letters indicate values that are significantly different from each other (p<0.05).

(FIG. 3A) Cumulative calcium and (FIG. 3B) phosphate ion concentrations. Each value is mean±sd (n=6).

(FIG. 12A) Orthodontic bracket shear bond strength (mean±sd; n=10). (FIG. 12B) Adhesive Remnant Index for the debonded specimens according to the following scales: 0=no adhesive left on the tooth surface; 1=less than half of the adhesive was left on the tooth surface; 2=half or more of the adhesive was left on the tooth; 3=the entire adhesive was left on the tooth surface. In each blot, bars with dissimilar letters indicate values that are significantly different from each other (p<0.05).

(FIG. 13A) Ca ion release. (FIG. 13B) $PO_4$ ion release. PEHB+40% NACP showed the significant higher Ca and $PO_4$ ion release than those of PE+40% NACP (p<0.05).

(FIG. 14A) Ca ion re-release. (FIG. 14B) $PO_4$ ion re-release. Ca and P ion re-release of PEHB+40% NACP were significantly higher than that of PE+40% NACP (p<0.05). There was no decrease in the re-release level with increasing the recharge/re-release cycle from cycle 1 to 3 (p>0.1).

DETAILED DESCRIPTION

Figure 1:
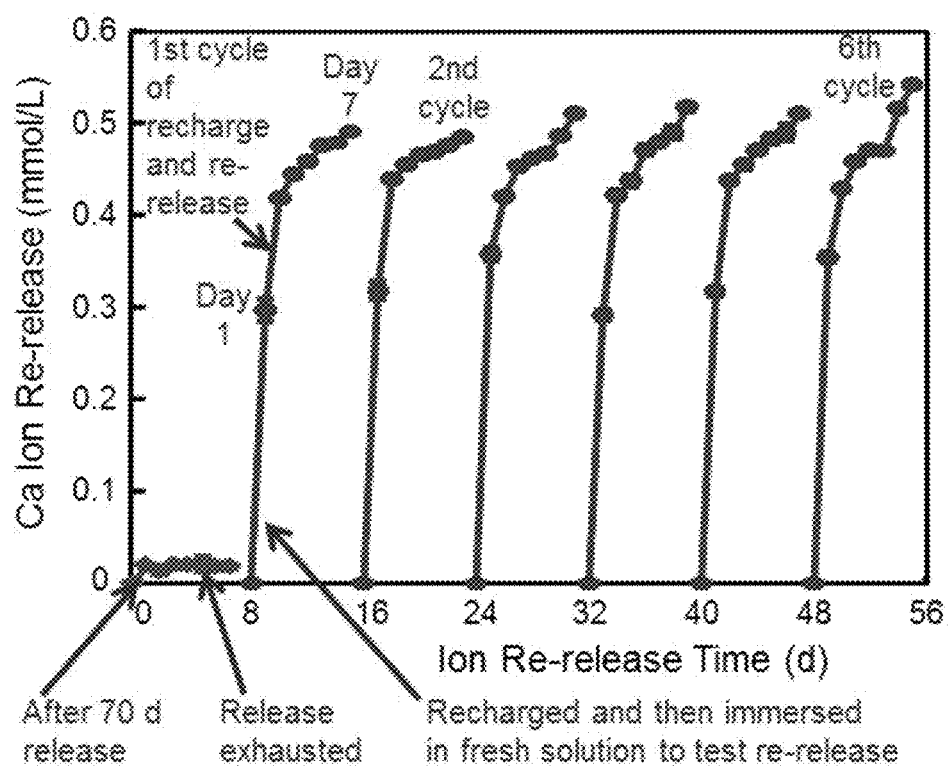
FIG. 1. Illustration of Ca and P recharge and re-release. NACP nanocomposite was first immersed in a pH 4 solution for 70 days (hereinafter days is abbreviated as "d") to exhaust the ion release, as indicated by the lower left arrow. Then the specimens were immersed in a new pH 4 solution to confirm that the ion release was exhausted, as indicated by the lower middle arrow. The exhausted specimens were recharged in a recharge solution. The specimens were then tested for Ca and P ion re-release for 7 d, as indicated by the third arrow at the bottom of FIG. 1. This constituted the first recharge/re-release cycle. This process was repeated for 6 cycles.

The development of calcium phosphate (CaP) dental composites that can release calcium (Ca) and phosphate (P) ions has been recognized as a promising approach to combat tooth caries [7-13]. Traditional CaP composites contained CaP particles with sizes of 1-55 μm and achieved successful remineralization of tooth lesions [7,9,10]. Re-incorporation of minerals into the demineralized dentin matrix is important since the precipitated mineral may serve as sites for further nucleation, and the remineralized tissues may be more resistant to degradation [14].

Recently, nanocomposites containing nanoparticles of amorphous calcium phosphate (NACP) with a mean particle size of 116 nm were developed [13,15-17]. These NACP nanocomposites were found to release high levels of Ca and P ions while having mechanical properties 2-fold greater than those of traditional CaP composites [11,13]. They can rapidly neutralize lactic acid solutions at a cariogenic pH of 4 and increase the pH to a safe level of above 6 [15]. These nanocomposite can also successfully remineralize enamel lesions in vitro, achieving a remineralization that is 4-fold greater than that of a commercial fluoride-releasing composite [16]. In a human in situ model, NACP nanocomposites inhibited secondary caries at the enamel-restoration margins in vivo, reducing the enamel mineral loss at the margins to ⅓ of the mineral loss associated with a control composite without NACP [17].

However, a major drawback of CaP composites is that the Ca and P ion release lasts for only weeks to months, thus diminishing over time. Previous studies measured Ca and P ion release from composites to, at most, a couple of months [7,9,13,16,18]. However, clinicians and patients would expect the composite restorations to be effective in vivo for much longer than a few months (e.g., for 10 or 20 years).

In light of the problems with existing CaP composites, new rechargeable calcium phosphate-based dental materials, including dental adhesives, cements, composites, bonding agents, sealants and the like comprising these materials, were prepared and they are described herein. These rechargeable, calcium phosphate-based dental materials can be repeatedly recharged for indefinite and uninterrupted release of calcium and phosphate ions from the materials. These rechargeable dental materials contain calcium phosphate nanoparticles and tailored rechargeable monomers that together form compositions that provide the unique recharge and release capabilities.

The rechargeable calcium phosphate-based dental materials of the present invention can be included in a variety of dental applications including tooth caries restoration, orthodontic applications, crown construction, inlay/onlay applications, and tooth and root coatings, to name only a few.

The rechargeable dental materials of the invention can be used in the preparation of a number of different dental products including, but not limited to, primers, resins, bases, liners, adhesives, cements (such as orthodontic cements, crown cements, and inlay/onlay cements), composites (such as flowable composites, low-shrinkage composites, non-shrinking composites), bonding agents, sealants (such as pit and fissure sealants), varnishes, and coatings (such as tooth coatings and root surface coatings), each of which is rechargeable for Ca and/or P ion release.

1. Rechargeable Dental Materials

The basis of the present invention is the rechargeable, calcium phosphate-based dental materials (also termed more succinctly "rechargeable dental materials" or "RDMs" herein) defined herein. These materials can be used in the production of each of the other dental products described herein, e.g., primers, resins, bases, liners, adhesives, cements (such as orthodontic cements, crown cements, and inlay/onlay cements), composites (such as flowable composites, low-shrinkage composites, non-shrinking composites), bonding agents, sealants (such as pit and fissure sealants), varnishes, and coatings (such as tooth coatings and root surface coatings), each of which is rechargeable for Ca and/or P ion release.

The rechargeable dental materials of the present invention comprise (i) one or more rechargeable monomers and (ii) nanoparticles of amorphous calcium phosphate (NACP). As described below additional components can be included in the RDMs, depending on the particular dental product in which they are used and the application to which the dental product is put.

1a. Rechargeable Monomers

Careful selection of the particular rechargeable monomers that are used to prepare the rechargeable dental materials can greatly increase the ability of the compositions comprising the monomers to be recharged with Ca and P ions. While the RDMs can comprise a single species of monomer, in certain aspects the rechargeable dental materials contain two or more, three or more, or four or more different rechargeable monomers. In other aspects, the rechargeable dental materials contain 1, 2, 3, 4 or more different rechargeable monomers.

Suitable rechargeable monomers will be those monomers commonly used in dental applications or that would be suitable for dental applications. Such monomers typically comprise a matrix that is of a hardenable dental polymer. Exemplary monomers include bisphenol glycidyl methacrylate (bis-GMA), triethylene glycol dimethacrylate (TEGDMA), 2-hydroxyethyl methacrylate (HEMA), urethane dimethacrylate (UDMA), pyromellitic acid glyceryl dimethacrylate (PMGDM), ethoxylated bisphenol A dimethacrylate (EBPADMA), Bis[2-(methacryloyloxy)ethyl] phosphate (BisMEP), methacryloyloxyethyl phthalate (MEP), methacrylate-modified polyalkenoic acid, pyromellitic dimethacrylate (PMDM), glycerol dimethacrylate/maleate adduct, glycerol dimethacrylate/succinate adduct, 2-acetoacetoxyethyl methacrylate, and methacryloyloxyethyl maleate. Other suitable monomers include those of the following that can be recharged for Ca and/or P ion content: a hydrophobic monomer, a hydrophilic monomer, a poly acid-modified polymer, a light-cured polymer, a self-cured polymer, a duel cured polymer and a heat-cured polymer.

In certain aspects, the one or more rechargeable monomers in the rechargeable dental materials are Bis-GMA and TEGDMA at 1:1 mass ratio. In another aspect, the one or more rechargeable monomers are PMGDM and EBPADMA at a mass ratio ranging from 1:1 to 2:1. In yet another aspect, the one or more rechargeable monomers are Bis-GMA, TEGDMA, and BisMEP at mass ratios that include 2:1:1, 2:0.5:1.5, 3:1:1, and 3:1:2. In another aspect, the one or more rechargeable monomers are PMGDM, EBPADMA and HEMA. In a further aspect, the one or more rechargeable monomers are PMGDM, EBPADMA, HEMA, and Bis-GMA.

The combined amount of the one or more rechargeable monomers in the rechargeable dental materials is about 0.5% to about 90% of the mass of the rechargeable dental material. In certain aspects, the combined amount of the one or more rechargeable monomers in the rechargeable dental material is from about 10% to about 90%, from about 10% to about 85%, from about 10% to about 80%, from about 10% to about 75%, from about 10% to about 70%, from about 10% to about 65%, from about 10% to about 60%, from about 10% to about 55%, from about 10% to about 50%, from about 20% to about 90%, from about 20% to about 85%, from about 20% to about 80%, from about 20% to about 75%, from about 20% to about 70%, from about 20% to about 65%, from about 20% to about 60%, from about 20% to about 55%, from about 20% to about 50%, from about 30% to about 90%, from about 30% to about 86%, from about 30% to about 80%, from about 30% to about 75%, from about 30% to about 70%, from about 30% to about 65%, from about 30% to about 60%, from about 40% to about 55%, from about 30% to about 50%, from about 40% to about 90%, from about 40% to about 88%, from about 40% to about 80%, from about 40% to about 75%, from about 40% to about 70%, from about 40% to about 65%, from about 40% to about 60%, from about 40% to about 55%, from about 40% to about 50% of the mass of the rechargeable dental material.

1b. NACP

As indicated above, the rechargeable dental materials of the present invention include nanoparticles of amorphous calcium phosphate NACP. NACP comprises nanometer-sized amorphous calcium phosphate ($Ca_3[PO_4]_2$) particles. The use of NACP results in dental materials with high Ca and $PO_4$ release, excellent mechanical properties, and antibacterial properties. Dental materials that include NACP exhibit greatly increased ion release at acidic, cariogenic pH, when these ions are most needed to inhibit caries.

The NACP may make up between about 1% and about 90% of the mass of the rechargeable dental materials. In certain aspects, the NACP is from about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, about 30% to about 90%, about 30% to about 85%, about 30% to about 80%, about 30% to about 75%, about 30% to about 70%, about 30% to about 65%, about 30% to about 60%, about 30% to about 55%, about 30% to about 50%, about 30% to about 45%, or about 30% to about 40% of the mass of the rechargeable dental material.

The NACP particles may range in size from about 10 nm to about 1000 nm. In certain aspects, the NACP particles range in size from about 10 nm to about 500 nm, about 50 nm to about 750 nm, about 50 nm to about 500 nm, about 75 nm to about 700 nm, about 75 nm to about 3000 nm, about 100 nm to about 200 nm, or about 125 nm to about 200 nm. In other aspects, the size of the NACP particles averages about 75, 80, 85, 90, 95, 100, 105, 110, 115, 120, 125, 130, 135, 140, 145, 150, 155, 160, 165, 170, 175, 180, 185, 190, 195 or 200 nm. In further aspects, the size of the NACP particles is about 160 nm to about 170 nm. In other aspects, the size of the NACP particles average 116 nm. In yet another aspect, the size of the NACP particles average 166 nm.

The NACP particles have a relatively high specific surface area. The NACP particles have a specific surface area of about 2-206 $m^2/g$. In certain aspects, the NACP particles have a specific surface area of about 3-150 $m^2/g$, 4-100 $m^2/g$, 5-75 $m^2/g$, 6-50 $m^2/g$, or 10-25 $m^2/g$. In a certain aspect, the NACP particles have a specific surface area of about 15-20 $m^2/g$. In a further aspect, the NACP particles have a specific surface area of about 17.75 $m^2/g$.

1c. Acidic Methacrylate and Acrylate-Based Monomers

In addition to the one or more rechargeable monomers listed above, the rechargeable dental materials may include one or more acidic methacrylate and acrylate-based monomers that have the potential for calcium and phosphate recharge. These monomers can be divided by their corresponding acidic functional groups: (1) carboxylic acid, (2) phosphonic acid, and (3) sulfonic acid. Monomers from each of these groups may be used to recharge calcium and phosphate ions in the same manner that PMGDM (carboxylic acid functionality) and MEP (phosphonic acid functionality) have been shown to recharge as described herein.

Suitable carboxylic acid-based monomers include, but are not limited to, pyromellitic dimethacrylate (PMDM) [25], methacryloyloxyethyl phthalate [25], methacryloyloxyethyl maleate [26], 2-hydroxyethyl methacrylate/succinate [19], glycerol dimethacrylate/maleate adduct [24], glycerol dimethacrylate/sucinate adduct [24], mono-2-(methacryloyloxy) ethyl maleate (CAM) [22], 4-methacryloyloxyethyl trimellitic acid (4-MET) [23], 10-methacryloyloxydecyl malonic acid (MAC-10) [23], N-methacryloyl-1-aminosalicylic acid (MASA) [23], N-methacryloyl glycine (NMGLY) [23], biphenyl dimethacrylate or 4,4'-dimethacryloyloxyethyl-oxycarbonylbiphenyl-3,3'-dicarboxylic acid (BPDM) [25], butan-1,2,3,4-tetracarboxylic acid di-2-hydroxyethylmethacrylate ester (TCB) [25], ortho-(N-methacryloyl amino) benzoic acid (o-MABA) [21], meta-(N-methacryloyl amino) benzoic acid (m-MABA) [21], para-(N-methacryloyl amino) benzoic acid (p-MABA) [21], 2-(N-methacryloyl amino) terephthalic acid (2-MATPA) [21], 5-(N-methacryloyl amino) isophthalic acid (5-MAIPA) [21], and 4-methacryloxy phthalic acid (4-MPA) [21].

Suitable phosphonic acid-based monomers include, but are not limited to, 2-hydroxyethyl methacrylate phosphate [25], 10-Methacryloyldecyl Dihydrogen Phosphate (MDP) [25], 1,3-glycerol dimethacrylate phosphate (PAM) [22], Glycerol dimethacrylate ester of phosphoric acid (GDMP) [23], methacryloyloxyethyl phenyl hydrogen phosphate (MEP-P) [23], methacryloyloxypropyl dihydrogen phosphate (MPP) [23], dipentaerythrolpentaacryloyl dihydrogen phosphate (PENTA-P) [23], vinylphosphonic acid (VPA) [23], 4-vinylbenzylphosphonic acid (VBPA) [23], ethyl 2-[4-(dihydroxyphosphoryl)-2-oxabutyl]acrylate (EAEPA) [23], (2,4,6-trimethylphenyl 2-[4-(dihydroxyphosphoryl)-2-oxabutyl]acrylate (MAEPA) [23], 2-[4-(dihydroxyphosphoryl)-2-oxabutyl]acrylonitrile (NAEPA) [23], and 2-[4-(dihydroxyphosphoryl)-2-oxabutyl]acrylic acid (CAEPA) [23].

Suitable sulfonic acid-based monomers include, but are not limited to, 2-acrylamido-2-methylpropane sulfonic acid [23], and 2-sulfoethyl methacrylate [20].

The combined amount of the one or more acidic methacrylate and acrylate-based monomers in the rechargeable dental materials is about 1% to about 50% by mass of the rechargeable dental material. In certain aspects, the combined amount of the one or more acidic methacrylate and acrylate-based monomers in the rechargeable dental material is from about 1% to about 40%, from about 2.5% to about 50%, from about 2.5% to about 45%, from about 2.5% to about 40%, from about 2.5% to about 35%, from about 2.5% to about 30%, from about 2.5% to about 25%, from about 2.5% to about 20%, from about 2.5% to about 15%, from about 5% to about 50%, from about 5% to about 45%, from about 5% to about 40%, from about 5% to about 35%, from about 5% to about 30%, from about 5% to about 25%, from about 5% to about 20%, from about 5% to about 15%, from about 7.5% to about 50%, from about 7.5% to about 45%, from about 7.5% to about 40%, from about 7.5% to about 35%, from about 7.5% to about 30%, from about 7.5% to about 25%, from about 7.5% to about 20%, from about 7.5% to about 15%, from about 7.5% to about 12.5%, from about 10% to about 50%, from about 10% to about 45%, from about 10% to about 40%, from about 10% to about 35%, from about 10% to about 30%, from about 10% to about 25%, from about 10% to about 20%, or about 40% to 50% of the mass of the rechargeable dental materials.

1d. Antibacterial Agents

The rechargeable dental materials of the present invention may further comprise one or more antibacterial agents including, but not limited to, antibacterial monomers, quaternary ammonium salts (QAS), silver-containing nanoparticles (NAg), chlorhexidine particles, TiO2 particles and ZnO particles.

Suitable antibacterial monomers have alkyl chains of varying lengths. The antibacterial monomers include one or more of dimethylamino propyl methacrylate (DMAPM), dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMADDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), and dimethylamino docosyl methacrylate (DMADOM). These antibacterial monomers are well suited for use in rechargeable dental materials that are used in the production of dental products, such as dental composites.

When present, the amount of antibacterial monomers in the rechargeable dental material is a combined amount of antibacterial monomers of from about 0.5% to about 50% of the mass of the rechargeable dental material. In certain aspects, the combined amount of the antibacterial monomers is from about 1% to about 25%, from about 2.5% to about 25%, from about 2.5% to about 20%, from about 2.5% to about 15%, from about 5% to about 25%, from about 5% to about 20%, from about 5% to about 15%, from about 7.5% to about 25%, from about 7.5% to about 20%, about 7.5% to about 15%, or from about 7.5% to about 12.5% of the mass of the rechargeable dental materials.

Suitable QASs include both polymerizable monomers and non-polymerizable small molecules, and include, but are not limited to, bis(2-methacryloyloxy-ethyl) dimethyl-ammonium bromide (QADM), methacryloyloxydodecylpyridinium bromide, methacryloxyethyl benzyl dimethyl ammonium chloride, methacryloxyethyl m-chloro benzyl dimethyl ammonium chloride, methacryloxyethyl cetyl dimethyl ammonium chloride, cetylpyridinium chloride, and methacryloxyethyl cetyl ammonium chloride, QAS chlorides, QAS bromides, QAS monomethacrylates, QAS dimethacrylates, and pre-fabricated QAS particles. Please see U.S. Pat. No. 8,889,196, which is incorporated by reference herein in its entirety. When present, the QAS may make up between about 1% and about 30% of the mass of the rechargeable dental material. In certain aspects, the QAS will make up between about 2% and about 25%, about 5% and about 20%, or about 7.5% and about 15% of the mass of the rechargeable dental material, or about 1%, 2.5%, 5%, 7.5%, 10%, 12.5, 15%, 17.5%, 20%, 22.5%, 25%, 27.5% or 30% of a mass fraction of the rechargeable dental material.

Suitable NAg include, but are not limited to, silver 2-ethylhexanoate salt, silver-containing glass particles and silver benzoate. In addition to silver salts, pre-formed silver nanoparticles can be used. When present, NAg may make up between about 0.01% and about 20% of the mass of the rechargeable dental material. In certain aspects, NAg will make up between about 0.05% and about 5%, or 0.08% and about 10%, of the mass of the rechargeable dental material, or about 0.01%, 0.08%, 0.15%, 0.20%, 0.25%, 0.30%, 0.35%, 0.40%, 0.45%, 0.50%, 1.0%, 1.5%, 2.0%, 2.5%, 3.0%, 3.5%, 4.0%, 4.5% or 5.0% of the mass of the rechargeable dental material. In one aspect, NAg makes up about 0.08% of the mass of the rechargeable dental material. The silver particle size can range from about 1 nm to about 1000 nm, and in one aspect, from about 2 nm to about 500 nm.

1e. Protein Repellant Materials

The rechargeable dental materials of the present invention may further comprise one or more protein-repellent agents. The protein-repellent agents inhibit adsorption of bacteria to the dental products, thereby enhancing their anti-cariogenic properties. Suitable protein-repellant agents include 2-methacryloyloxyethyl phosphorylcholine (MPC), poly(hydroxyethyl methacrylate) (HEMA) and derivatives thereof, and poly(N-isopropylacrylamide) and derivatives thereof. The amount of protein-repellant agent in the rechargeable dental materials ranges from about 0.5% to about 50% of the mass of the rechargeable dental material. In certain aspects, the range is from about 1% to about 25%, about 2.5% to about 20%, about 4% to about 15%, or about 5% to about 12.5% of the mass of the rechargeable dental material. In certain aspects, the amount of protein-repellant agent is about 2.5%, 3%, 3.5%, 4%, 4.5%, 5%, 5.5%, 6%, 6.5%, 7%, 7.5%, 8%, 8.5%, 9%, 9.5%, or 10% of the mass of the rechargeable dental material.

1f. Curing Agents

The one or more rechargeable monomers used in the rechargeable dental materials of the invention may be rendered light-curable or chemically curable through the inclusion of appropriate curing agents to the rechargeable dental materials. For example, camphorquinone (CQ), ethyl 4-N, N-dimethylaminobenzoate, phenylbis (2,4,6-triemthylbenzoyl) phosphine oxide, or combinations thereof may be included in the RDM, rendering the rechargeable monomers light-curable. In another example, benzoyl peroxide (BPO) may be included in the RDM, rendering the rechargeable monomers chemically-curable. In yet another example, one or more light-curable compounds and one or more chemical-curable compounds may be included in the RDM. In a particular example, about 0.2% CQ and about 0.8% ethyl 4-N,N-dimethylaminobenzoate may be included in the RDM to render the resulting material light-curable. In another example, 1% phenylbis (2,4,6-triemthylbenzoyl) phosphine oxide may be included in the RDM to render the resulting material light-curable. In further example, CQ and BPO may be included in the RDM to render the resulting material light-curable and chemically-curable.

2. Rechargeable Dental Adhesives

Calcium phosphate-based dental adhesives with Ca and P ion releasing activity can also remineralize tooth lesions and inhibit caries. Therefore, the rechargeable dental adhesives of the present invention were also developed.

The rechargeable dental adhesives of the invention comprise (i) the rechargeable dental materials defined herein and (ii) one or more curing agents. Suitable curing agents include camphorquinone (CQ), ethyl 4-N,N-dimethylaminobenzoate, and phenylbis (2,4,6-triemthylbenzoyl) which are light-curable agents, and enzoyl peroxide (BPO) which is a chemically-curable agent. The rechargeable dental adhesives may include one or more light-curable compounds, one or more chemically-curable compounds, or both one or more light-curable compounds and one or more chemically-curable compounds.

The amount of curing agent that is included in the rechargeable dental adhesives of the invention is a combined amount of curing agents ranging from about 0.05% to about 5% of the mass of the rechargeable dental adhesive. In certain aspects, the combined amount of the curing agents is from about 0.1% to about 5%, from about 0.2% to about 5%, from about 0.3% to about 5%, from about 0.4% to about 5%, from about 0.5% to about 5%, from about 0.6% to about 5%, from about 0.7% to about 5%, from about 0.8% to about 5%, from about 0.9% to about 5%, from about 1% to about 5%, from about 1.1% to about 5%, from about 1.2% to about 5%, from about 1.3% to about 5%, from about 1.4% to about 5%, from about 1.5% to about 5%, from about 1.6% to about 5%, from about 1.7% to about 5%, from about 1.8% to about 5%, from about 1.9% to about 5%, or from about 2% to about 5% of the mass of the rechargeable dental adhesive.

The amount of the rechargeable dental material that is included in the rechargeable dental adhesives of the invention ranges from about 95% to about 99.95% of the mass of the rechargeable dental adhesive.

In a particular example, about 0.2% CQ and about 0.8% ethyl 4-N,N-dimethylaminobenzoate may be included in the rechargeable dental adhesive to render the resulting adhesive light-curable. In another example, 1% phenylbis (2,4,6-triemthylbenzoyl) phosphine oxide may be included in the rechargeable dental adhesive to render the resulting adhesive light-curable. In further example, CQ and BPO may be included in the rechargeable dental adhesive to render the resulting adhesive light-curable and chemically-curable.

A suitable combination of rechargeable monomers for a rechargeable dental material for use in a rechargeable dental adhesive is PMGDM and EBPADMA. In another example, a suitable combination is PMGDM, EBPADMA and HEMA. In yet another example, a suitable combination is PMGDM, EBPADMA, HEMA and Bis-GMA.

The amount of NACP included in the rechargeable dental material for use in a rechargeable dental adhesive includes between about 5% to about 60%, about 10% to about 50%, about 10% to about 40%, about 20% to about 40%, about 20% to about 35%, about 20% to about 30%, about 25% to about 40%, and about 25% to about 35% by mass of the rechargeable dental material. In a certain aspect, NACP is present in the rechargeable dental material in an amount of about 20, 25, 30, 35 or 40% by mass.

The rechargeable dental adhesives of the application may be used in conjunction with a primer and/or an etchant. A suitable primer composition may be added to the tooth of a subject prior to the application of the rechargeable dental adhesive. Such a primer composition may include PMGDM and HEMA in a mass ratio of 3.3:1 with a solvent. A suitable solvent may be acetone. Suitable etchants include phosphoric acid (35-40%). Also contemplated are kits comprising the rechargeable dental adhesives along with a primer and/or etchant.

Rechargeable dental adhesives encompassed within the scope of the claims include those provided in Table 1 that are discussed in the Examples below.

TABLE 1

Compositions (mass %) of experimental adhesives of the present study

| Adhesive | PMGDM | EBPADMA | HEMA | Bis-GMA | BAPO |
|---|---|---|---|---|---|
| PE | 49.5 | 49.5 | — | — | 1 |
| PEH | 44.5 | 44.5 | 10 | — | 1 |
| PEHB | 44.5 | 39.5 | 10 | 5 | 1 |

PMGDM: pyromellitic glycerol dimethacrylate (Hampford, Stratford, CT).
EBPADMA: ethoxylated bisphenol A dimethacrylate (Sigma-Aldrich, St, Louis, MO).
Bis-GMA: bisphenol A glycidyl dimethacrylate (Esstech, Essington, PA).
HEMA: 2-hydroxyethyl methacrylate (Esstech, Essington, PA).
BAPO: phenylbis (2,4,6-trimethylbenzoyl) phosphine oxide (Esstech, Essington, PA).

The rechargeable dental materials used in the production of the rechargeable dental adhesives may include any of the additional components described above, including acidic methacrylate and acrylate-based monomers, antibacterial agents, and protein-repellent agents. Thus, the rechargeable dental materials as defined herein can be used in the production of the rechargeable dental adhesives of the invention.

3. Rechargeable Dental Cements

Rechargeable dental cements containing NACP were also developed as part of the present invention. As discussed in the examples, these cements exhibit high bracket shear bond strength and Ca and P ion release capabilities when used in orthodontic applications. These cements are promising candidates for inhibiting demineralization and formation of white spot lesions (WSLs) around bonded brackets.

The rechargeable dental cements of the invention are similar in composition to the rechargeable dental adhesives defined above in that they also comprise (i) the rechargeable dental materials defined herein and (ii) one or more curing agents. However, dental cements are thicker and more viscous than adhesives, and they form a thicker layer in the restoration than adhesives.

Suitable curing agents include camphorquinone (CQ) which is a light-curable agent, and enzoyl peroxide (BPO) which is a chemically-curable agent. The rechargeable dental cements may include one or more light-curable compounds, one or more chemically-curable compounds, or both one or more light-curable compounds and one or more chemically-curable compounds.

The amount of curing agent that is included in the rechargeable dental cements of the invention is a combined amount of curing agent ranging from about 0.05% to about 5% of the mass of the rechargeable dental cement. In certain aspects, the combined amount of the curing agents is from about 0.1% to about 5%, from about 0.2% to about 5%, from about 0.3% to about 5%, from about 0.4% to about 5%, from about 0.5% to about 5%, from about 0.6% to about 5%, from about 0.7% to about 5%, from about 0.8% to about 5%, from about 0.9% to about 5%, from about 1% to about 5%, from about 1.1% to about 5%, from about 1.2% to about 5%, from about 1.3% to about 5%, from about 1.4% to about 5%, from about 1.5% to about 5%, from about 1.6% to about 5%, from about 1.7% to about 5%, from about 1.8% to about 5%, from about 1.9% to about 5%, or from about 2% to about 5% of the mass of the rechargeable dental cement.

The amount of the rechargeable dental material that is included in the rechargeable dental cements of the invention ranges from about 95% to about 99.95% of the mass of the rechargeable dental cement.

A suitable combination of rechargeable monomers for a rechargeable dental material for use in a rechargeable dental cement of the invention is PMGDM and EBPADMA. In another example, a suitable combination is PMGDM, EBPADMA and HEMA. In yet another example, a suitable combination is PMGDM, EBPADMA, HEMA and Bis-GMA.

The amount of NACP included in the rechargeable dental material for use in a rechargeable dental cement of the invention includes between about 5% to about 60%, about 10% to about 50%, about 15% to about 45%, about 20% to about 45%, about 30% to about 50%, about 30% to about 45%, about 30% to about 40%, about 35% to about 50%, and about 35% to about 45% by mass of the rechargeable dental material. In a certain aspect, NACP is present in the rechargeable dental material in an amount of about 30, 35, 40, 45, or 50% by mass.

The rechargeable dental cement of the application may be used in conjunction with a primer and/or an etchant. A suitable primer composition may be added to the tooth of a subject prior to the application of the rechargeable dental cement. Such a primer composition may include PMGDM and HEMA in a mass ratio of 3.3:1 with a solvent. A suitable solvent may be acetone. Suitable etchants include 35-40% phosphoric acid. Also contemplated are kits comprising the rechargeable dental cements along with a primer and/or etchant.

Rechargeable dental cements encompassed within the scope of the claims include those provided in Table 2 that are discussed in the Examples below.

TABLE 2

Composition (% by mass) of resin matrices of cements in the study

| Experimental | Liquid | | | | Powder | |
|---|---|---|---|---|---|---|
| cements | PMGDM | EBPADMA | HEMA | Bis-GMA | BPO | CQ |
| PE | 49.5 | 49.5 | — | — | 0.8 | 0.2 |
| PEHB | 44.5 | 39.5 | 10 | 5 | 0.8 | 0.2 |

PMGDM: pyromellitic glycerol dimethacrylate (Hampford, Stratford, CT); EBPADMA: ethoxylated bisphenol A dimethacrylate (Sigma-Aldrich, St, Louis, MO); Bis-GMA: bisphenol A glycidyl dimethacrylate (Esstech, Essington, PA); HEMA: 2-hydroxyethyl methacrylate; CQ: camphorquinone (Irgacure819, Ciba Chemicals, Japan); BPO: benzoyl peroxide (BPO) (Irgacure819, Ciba Chemicals, Japan).

The rechargeable dental materials used in the production of the rechargeable dental cements may include any of the additional components described above, including acidic methacrylate and acrylate-based monomers, antibacterial agents, and protein-repellent agents. Thus, the rechargeable dental materials as defined herein can be used in the production of the rechargeable dental cements of the invention.

4. Rechargeable Dental Composites

Calcium phosphate (CaP) dental composites with Ca and P ion release can remineralize tooth lesions and inhibit caries. However, ion release diminishes over time. Rechargeable dental composites containing NACP were therefore also developed as part of the present invention.

The rechargeable dental composites of the invention comprise (i) the rechargeable dental materials defined herein and (ii) one or more fillers. The fillers increase the strength of the composite. Suitable fillers include one or more of glass fillers, ceramic fillers, and polymer-based fillers. In some instances, additional NACP can be include as the filler or one of the fillers.

Particular examples of suitable glass fillers include barium boroaluminosilicate, strontium-alumino-fluoro-silicate glass, silicon dioxide, fluoroaluminosilicate glass, a ytterbium tri-fluoride filler, and a fiber glass filler. Particular examples of suitable ceramic fillers include any dental ceramic such as a porcelain filler, a quartz filler, and a zirconia filler. Polymer-based filler includes dental polymer that is pre-polymerized and then ground into filler particles, and polymer fibers.

The combined amount of filler present in the rechargeable dental composites of the invention may vary, but the filler will generally comprise about 5% to about 90% of the mass of the rechargeable dental composite. In certain aspects, the combined amount of filler will comprise about 10% to about 85%, about 10% to about 80%, about 10% to about 70%, about 10% to about 60%, about 10% to about 50%, about 10% to about 40%, about 20% to about 80%, about 20% to about 70%, about 20% to about 60%, about 20% to about 50%, about 30% to about 80%, about 30% to about 70%, about 30% to about 60%, about 40% to about 80%, about 40% to about 70%, about 40% to about 60%, about 50% to about 80%, about 50% to about 70%, or about 45% to about 55% of the mass of the rechargeable dental composite. In certain other aspects, the filler is about 80%, about 75%, about 70%, about 65%, about 60%, about 55%, or about 50% of the mass of the rechargeable dental composite.

The size of the particles of the filler will depend on the identity of the filler or fillers. As an example, in an embodiment where barium boroaluminosilicate glass particles serve as the filler or one of fillers, the median particle diameter may be between about 0.1 and about 10 μm, or between about 1.0 μm and about 5 μm. Thus, the median particle diameter of the fillers used in the rechargeable dental composites of the present invention may be between about 0.1 and about 10 μm, or between about 1.0 μm and about 5 μm. In certain aspects, the median particle diameter of the filler may be about 0.6 μm, 0.8 μm, 1.0 μm, 1.2 μm, 1.4 μm, 1.6 μm, 1.8 μm, and 2.0 μm. The skilled artisan will understand that the particle size of the particular filler used will depend on the identity of the filler or fillers, and while the sizes provided here are with respect to barium boroaluminosilicate glass particles, similar sizes may pertain to one or more of the alternative fillers described herein.

Depending on the identity of the filler, the particles comprising the filler may be silanized. Suitable means for silanization are known to the skilled artisan and include, but are not limited to, a mixture of about 4% 3-methacryloxypropyltrimethoxysilane and about 2% n-propylamine. In one embodiment, the filler comprises barium boroaluminosilicate glass particles, where the particles are silanized. In another embodiment, the filler comprises silanized barium boroaluminosilicate glass particles having a median particle diameter of about 1.4 μm.

The amount of the rechargeable dental material that is included in the rechargeable dental composites ranges from about 10% to about 60% of the mass of the rechargeable dental cement. In certain aspects, the amount of the rechargeable dental material is from about 10% to about 55%, about 10% to about 50%, about 10% to about 45%, about 10% to about 40%, about 10% to about 35%, about 10% to about 30%, about 20% to about 60%, about 20% to about 55%, about 20% to about 50%, about 20% to about 45%, about 20% to about 40%, about 30% to about 60%, about 30% to about 55%, about 30% to about 50%, about 40% to about 60%, about 40% to about 55%, or about 40% to about 50% of the mass of the rechargeable dental composite. In certain other aspects, the filler is about 10%, about 15%, about 20%, about 25%, about 30%, about 35%, or about 40% of the mass of the rechargeable dental composite.

A suitable combination of rechargeable monomers for a rechargeable dental material for use in a rechargeable dental composite of the invention is Bis-GMA and TEGDMA at 1:1 mass ratio. In another aspect, a suitable combination is PMGDM and EBPADMA at a mass ratio ranging from 1:1 to 2:1. In yet another aspect, a suitable combination is Bis-GMA, TEGDMA, and BisMEP at mass ratios that include 2:1:1, 2:0.5:1.5, 3:1:1, and 3:1:2.

The amount of NACP included in the rechargeable dental material for use in a rechargeable dental composite of the invention includes between about 5% to about 60%, about 10% to about 50%, about 15% to about 45%, about 20% to about 50%, about 20% to about 45%, about 25% to about 55%, about 10% to about 25%, about 10% to about 20%, about 15% to about 30%, and about 15% to about 25% by mass of the rechargeable dental material. In a certain aspect, NACP is present in the rechargeable dental material in an amount of about 10, 15, 20, 25 or 30% by mass.

The rechargeable dental materials used in the production of the rechargeable dental composites may include any of the additional components described above, including acidic methacrylate and acrylate-based monomers, antibacterial agents, and protein-repellent agents. Thus, the rechargeable dental materials as defined herein can be used in the production of the rechargeable dental composites of the invention.

The rechargeable dental materials of the present invention and the dental products comprising these materials are suitable for use in oral applications in mammals, including primates such as human or non-human primates, and those of dogs, cats, horses, cattle, pigs, goats and sheep, for example.

5. Methods of Recharging Rechargeable Dental Material

The rechargeable dental materials and dental products comprising the materials described herein can be recharged by exposing the materials and products to calcium and phosphate ions. Thus, also described herein are methods of recharging the rechargeable dental materials and dental products comprising the materials with calcium ions, phosphate ions or combinations thereof.

To recharge the rechargeable dental materials, the dental products comprising the materials are exposed to a recharging composition comprising calcium ions, phosphate ions, or calcium and phosphate ions. Recharging the rechargeable dental materials means that the ions in the recharging composition bind or chelate to binding sites of the rechargeable monomers of the rechargeable dental materials. Upon being recharged, the rechargeable dental materials again contains Ca ion, P ions, or both, that then can continue to be released and provided to the tooth or teeth to which the dental products comprising the rechargeable dental materials have been applied.

Suitable, non-limiting examples of recharging compositions include a tooth paste, mouthwash, oral gel, gum, dental paste, and oral patch. The recharging composition may include compounds capable of providing Ca ions, such as $CaCl_2$, compounds capable of providing P ions, such as $KHPO_4$, or compounds or a mixture of compounds that can provide both Ca and P ions. The compounds that provide the desired ions (e.g., $CaCl_2$ and $KHPO_4$) in the recharging composition may be present in an amount ranging from about 2 mmol/L to about 50 mmol/L, about 5 mmol/L to about 40 mmol/L, about 10 mmol/L to about 30 mmol/L, or about 12 mmol/L to about 20 mmol/L.

The recharging composition may further comprise a buffer. The buffer may be present in an amount ranging from about 5 to about 100 mmol/L, about 10 to about 90 mmol/L, about 20 to about 80 mmol/L, about 30 to about 70 mmol/L, or about 40 to about 60 mmol/L. In certain aspects, the buffer is present in an amount of 50 mmol/L.

The recharging composition can be prepared in a manner that provides for conditions that promote the uptake of the ions by the rechargeable dental material. In this regard, the recharging composition may include pH adjusting additives. A pH of from about 5 to 12 will be suitable, and a pH of about 7 will generally provide the most suitable conditions that promote the uptake of the ions by the rechargeable dental materials.

During the recharging of the rechargeable dental material, the subject holds the recharging composition in the mouth for a period of time that will vary depending on the identity of the dental product comprising the material and the physical characteristics of the recharging composition. Suitable time periods range from about 10 seconds to about 24 hours. In certain aspects, the subject holds the recharging composition in the mouth for about 30 seconds to about 3 minutes. The recharge can be performed by a subject on a daily, weekly or monthly basis, or other suitable interval. The rechargeable dental material can continue to be recharged during the lifetime of the dental product comprising the rechargeable dental material.

After exposing the rechargeable dental material to the recharging composition, the rechargeable dental material is capable of providing calcium ions, phosphate ions or both calcium and phosphate ions to the surrounding tooth or teeth for a period of time that may range, e.g., from 1 day to 90 days after being recharged with ions. In certain aspects, the rechargeable dental material is capable of providing calcium ions, phosphate ions or both calcium and phosphate ions to the surrounding tooth or teeth about 7 to 14 days, about 7 to 21 days, about 7 to 28 days, about 7 to 35 days, about 7 to 42 days, 7 to 49, 7 to 56, or 7 to 63 days after being recharged with ions.

EXAMPLES

Example 1

Novel Rechargeable Calcium Phosphate Dental Nanocomposite

Three NACP nanocomposites were fabricated with resin matrix of: (1) bisphenol A glycidyl dimethacrylate (BisGMA) and triethylene glycol dimethacrylate (TEGDMA) at 1:1 mass ratio (referred to as the BisGMA group); (2) pyromellitic glycerol dimethacrylate (PMGDM) and ethoxylated bisphenol A dimethacrylate (EBPADMA) at 1:1 ratio (PMGDM group); (3) BisGMA, TEGDMA, and Bis [2-(methacryloyloxy)ethyl] phosphate (BisMEP) at 2:1:1 ratio (BisMEP group). Each resin was filled with 20% NACP and 50% glass particles, and the composite was photo-cured. Specimens were tested for flexural strength and elastic modulus, Ca and P ion release, and recharge and re-release.

NACP nanocomposites had strengths 3-4 fold of, and elastic moduli similar to, commercial resin-modified glass ionomer controls. The recharge capability was the greatest for PMGDM group, followed by BisMEP group, with BisGMA group the lowest ($p<0.05$). For each recharge cycle, the re-release reached similarly high levels, showing that the re-release did not decrease with more recharge cycles. After 6 recharge/re-release cycles, NACP nanocomposites without further recharge had continuous Ca and P release for 42 d. Details on the construction and testing of these rechargeable dental composites are provided in the following paragraphs.

NACP Nanocomposite Fabrication

NACP [$Ca_3(PO_4)_2$] nanoparticles were synthesized via a spray-drying technique as previously described [13,16]. Briefly, calcium carbonate and dicalcium phosphate anhydrous were dissolved into an acetic acid solution. The concentrations of Ca and P ions were 8 mmol/L and 5.333 mmol/L, respectively, yielding a Ca/P molar ration of 1.5. The solution was sprayed into a heated chamber to evaporate the water and volatile acid. The dried particles were collected by an electrostatic precipitator. A previously study showed that the NACP mean particle size was approximately 116 nm [13,16]. As a co-filler, barium boroaluminosilicate glass particles with a median size of 1.4 µm (Caulk/Dentsply, Milford, Del.) were silanized with 4% 3-methacryloxypropyltrimethoxysilane and 2% n-propylamine as previously described [13,16].

Three types of matrix resins were prepared to fabricate the NACP nanocomposite. For type 1, a resin of BisGMA and triethylene glycol dimethacrylate (TEGDMA) (Esstech, Essington, Pa.) at 1:1 mass ratio was rendered light-curable with 0.2% camphorquinone and 0.8% ethyl 4-N,N-dimethylaminobenzoate, following previous studies [13,16]. This is referred to as the BisGMA group.

For type 2, acidic monomer PMGDM and dimethacrylate EBPADMA (Sigma-Aldrich, St, Louis, Mo.) were mixed at a mass ratio of 1:1 to form the matrix resin [7,10]. This is referred to as the PMGDM group.

For type 3, BisGMA, TEGDMA, and acidic monomer BisMEP (Sigma-Aldrich) were mixed at a mass ratio of 2:1:1 to form the matrix resin [27]. This is referred as the BisMEP group.

The 0.2% camphorquinone and 0.8% ethyl 4-N,N-dimethylaminobenzoate were the same in all three groups.

Each aforementioned resin was filled with mass fractions of 20% NACP and 50% glass particles to form a readily-mixed and cohesive paste. Each composite paste was placed into a stainless steel mold of 2×2×25 mm, and light-cured (Triad 2000, Dentsply, York, Pa.) for 1 min on each open side. The specimens were stored at 37° C. for 24 h.

In addition, as commercial fluoride ion rechargeable controls, two RMGI cements were included in mechanical testing. A RMGI (Vitremer, 3M ESPE, St. Paul, Minn.) consisted of fluoroaluminosilicate glass, and a light-sensitive, aqueous polyalkenoic acid. According to the manufacturer, indications include Class III, V and root-caries restoration, Class I and II in primary teeth, and core-buildup. A powder/liquid ratio of 2.5/1 was used yielding a filler mass fraction of 71.4%, according to the manufacturer. Another RMGI (Ketac Nano, 3M) consisted of polycarboxylic acid modified with methacrylate groups and fluoroaluminosilicate glass, with a filler level of 69%. It is a two-part, paste/paste system and dispensed using the Clicker Dispensing System. It is recommended for small Class I restorations, and Class III and V restorations. All specimens were light-cured as described above and treated in the same manner.

Mechanical Testing

Five groups were tested for mechanical properties: the three NACP nanocomposite groups, and the two RMGIs as commercial rechargeable controls. Flexural strength and elastic modulus of specimens were measured using a three-point flexural test with a 10 mm span at a crosshead-speed of 1 mm/min on a computer-controlled Universal Testing Machine (5500R, MTS, Cary, N.C.) [13,18]. Flexural strength was calculated by: $S=3P_{max}/L(2bh^2)$, where $P_{max}$ is the fracture load, L is span, b is specimen width and h is thickness. Elastic modulus was calculated by: $E=(P/d)(L^3/[4bh^3])$, where load P divided by displacement d is the slope in the linear elastic region.

Ca and P Ion Release from NACP Nanocomposites

Three groups were tested for Ca and P ion release: BisGMA group, PMGDM group, and BisMEP group. The two RMGIs were not measured since this study investigated Ca and P ion release, not fluoride release. A sodium chloride (NaCl) solution (133 mmol/L) was buffered to pH 4 with 50 mmol/L lactic acid to measure ion release, simulating a cariogenic condition [13,17]. As in previous studies [8,13,17,18], three specimens of approximately 2×2×12 mm were immersed in 50 mL of solution to yield a specimen volume/solution of 2.9 $mm^3$/mL. This was similar to a specimen volume per solution of about 3.0 $mm^3$/mL in a previous study [9]. The concentrations of Ca and P ions released from the specimens were measured at 1, 3, 5, 7, 14, 21, 28, 35, 42, 49, 56, 63, and 70 days (d). At each time, aliquots of 0.5 mL were removed and replaced by fresh solution. The aliquots were analyzed for Ca and P ion concentrations via a spectrophotometric method (DMS-80 UV-visible, Varian, Palo Alto, Calif.) using known standards and calibration curves [7,9]. Six batches of specimens were tested and averaged for ion release for each group. The released ions were reported in cumulative concentrations [8,13,17,18]. This initial ion release from NACP nanocomposite was termed "virgin release", to differentiate from the subsequent recharge and re-release of ions.

Recharge of CaP Composite and Re-Release of Ions

The procedures of recharge and re-release measurement are illustrated in FIG. 1. First, NACP nanocomposite specimens were immersed in pH 4 solution to measure ion release as described above. At 70 d, the ion measurement showed that the ion concentration had plateaued and there was no further release. The composite specimens were removed from the 70-d solution and rinsed with water for 5 min. The specimens were then immersed in a flesh 50 mL solution at pH 4. Then Ca and P ion release was further measured for 7 d, which confirmed that the ion release was indeed exhausted and there was no further release, as indicated by the two arrows at the lower left corner in FIG. 1.

The exhausted specimens were then used for recharge. The recharging solutions for Ca and P ions were prepared respectively. The calcium ion recharging solution consisted of 20 mmol/L $CaCl_2$ and 50 mmol/L HEPES buffer [10,28]. The phosphate ion recharging solution consisted of 12 mmol/L $KHPO_4$ and 50 mmol/L HEPES buffer. Each solution was adjusted to a pH of 7.0 using 1 mol/L KOH [10,28]. Three specimens of approximately 2×2×12 mm were immersed in 5 mL of the calcium or phosphate solution and gently shaken on a mixing machine (Analog Vortex Mixer, Fisher Scientific, Waltham, Mass.) at a power level of 3 for 1 min. This immersion and shaking treatment simulated the movement in the mouth rinsing process when a calcium or phosphate mouth-rinse could be used. Then the specimens were rinsed with running distilled water for 1 min to remove any loosely attached deposits on specimen surfaces (hence only the ions recharged into the interior of the composite will be measured in the subsequent re-release test). This recharge process was repeated three times daily at 9:00 am, 12:00 noon and 5:00 pm for 3 d. All specimens for the BisGMA group, PMGDM group and BisMEP group were treated in the same manner for comparison of the recharge and re-release efficacy.

The recharged specimens were then immersed in 50 mL of the pH 4 solution as described above to measure Ca and P ion re-release, as indicated by the third arrow in the bottom of FIG. 1. In order to test the recharge/re-release cycle repeatedly for many times to investigate the durability, each cycle of re-release measurement lasted for 7 d (the short arrow in FIG. 1 indicates the measurement from 1 d to 7 d in the first cycle). After 7 d of re-release, the specimens were recharged again and tested for re-release, as cycle 2. This was repeated for 6 cycles in the present study as illustrated in FIG. 1.

After 6 cycles, in order to investigate how long the specimens could further release Ca and P ions, the specimens after the 6th cycle (without further recharge) were immersed in 50 mL of the pH 4 solution. The measurements of Ca and P ion release from these specimens were continued for an additional 42 d. At 1, 2, 3, 4, 5, 6, 7, 14, 21, 28, 35 and 42 d, the Ca and P measurements were again performed as described above. For each of the three NACP nanocomposite groups, three batches of specimens were tested and averaged for ion release following previous studies [8, 13,17,18].

Statistical Analysis

One-way and two-way analyses of variance (ANOVA) were performed to detect the significant effects of the variables. Tukey's multiple comparison tests were used to compare the data at a p value of 0.05.

Results

Figures 2A, 2B:
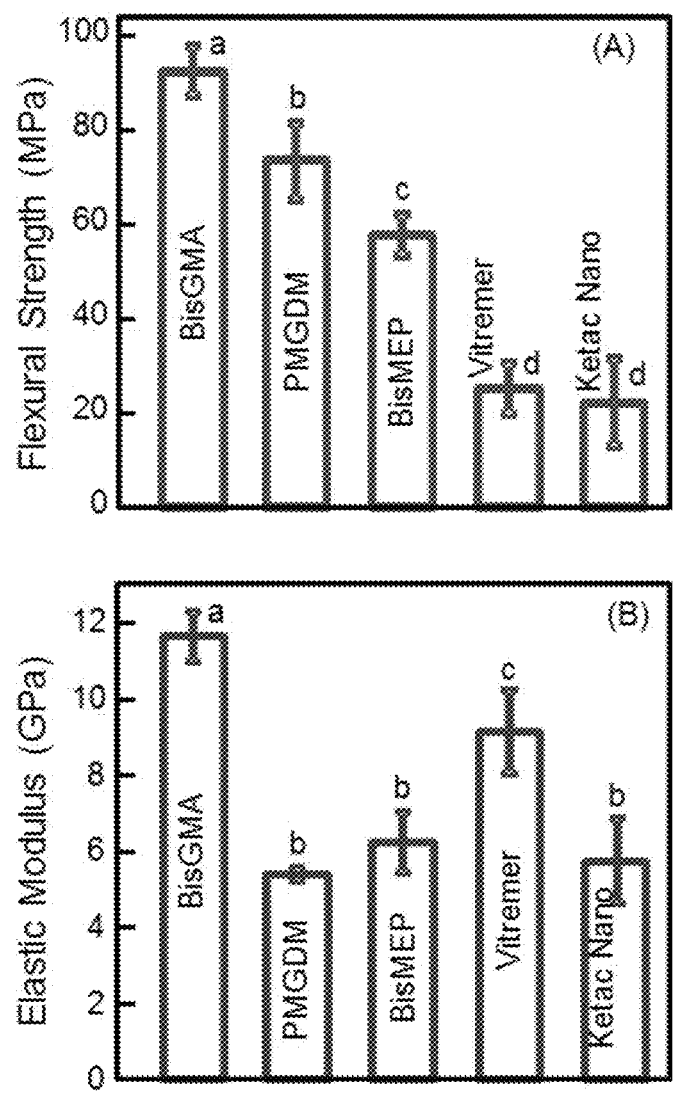
FIGS. 2A-2B. Mechanical properties.

FIG. 2 plots the flexural strength (FIG. 2A) and elastic modulus (FIG. 2B) of the three NACP nanocomposites and the two RMGI controls (mean±sd; n=6). The NACP nanocomposite of the BisGMA group showed the highest strength (p<0.05). All three NACP nanocomposites had strengths significantly higher than commercial controls (p<0.05). NACP nanocomposite of the BisGMA group had the greatest elastic modulus. NACP nanocomposites for the PMGDM and BisMEP groups had elastic moduli similar to that of Ketac Nano (p>0.1). These results showed that the NACP nanocomposites had strengths approximately 3-4 fold of, and elastic moduli generally similar to, those of commercial RMGI controls.

Figures 3A, 3B:
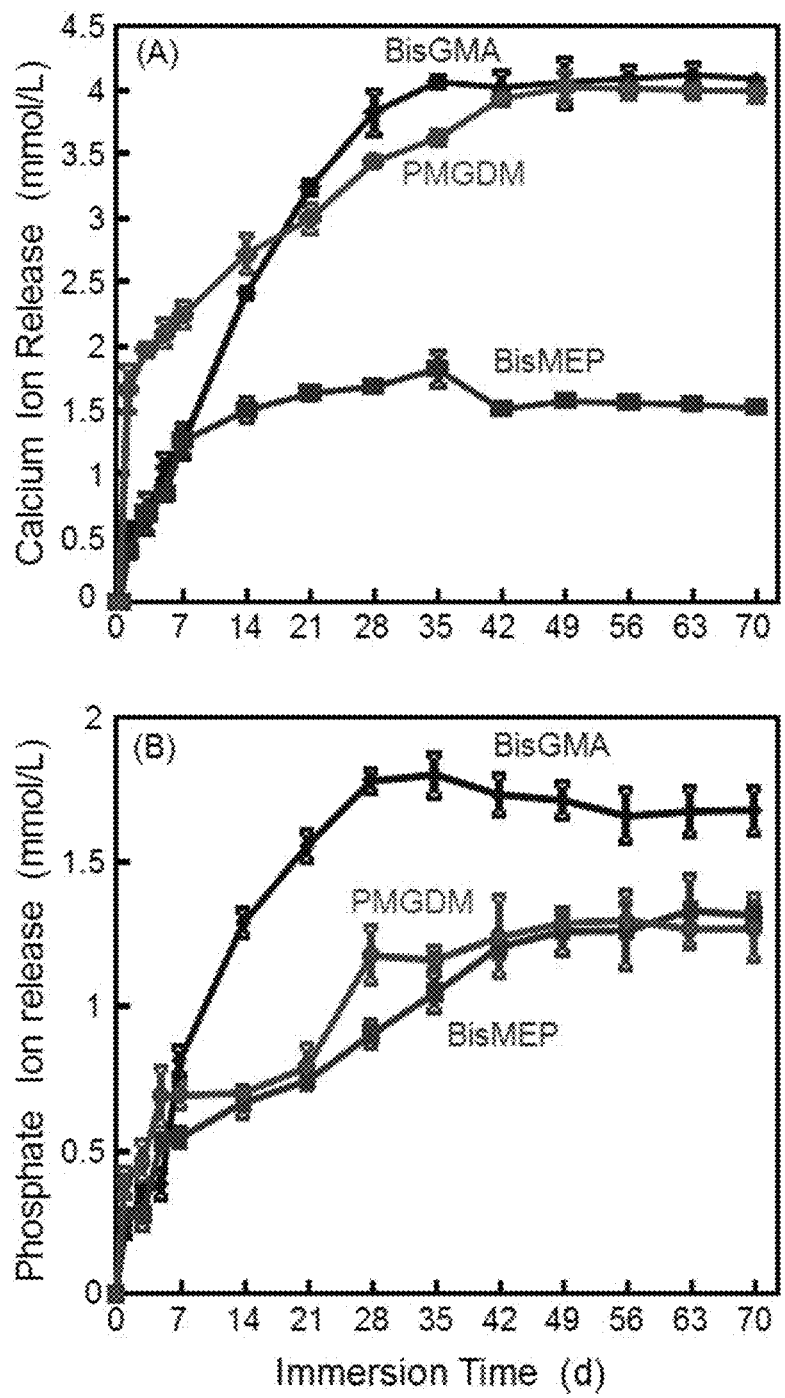
FIGS. 3A-3B. Calcium and phosphate ion release from virgin NACP nanocomposites.

NACP nanocomposites were tested for virgin release of Ca and P ions, and the results are plotted in FIG. 3 (mean±sd; n=6). Among the three groups, the Ca ion release (FIG. 3A) was relatively higher for the BisGMA and PMGDM groups, and lower for the BisMEP group. For P ion release (FIG. 3B), the PMGDM and BisMEP groups were similarly lower than the BisGMA group. For all three groups, the released ion concentrations increased with time, reaching a plateau at about 35 d to 42 d, indicating little further release from 42 d to 70 d.

Figures 4A, 4B:
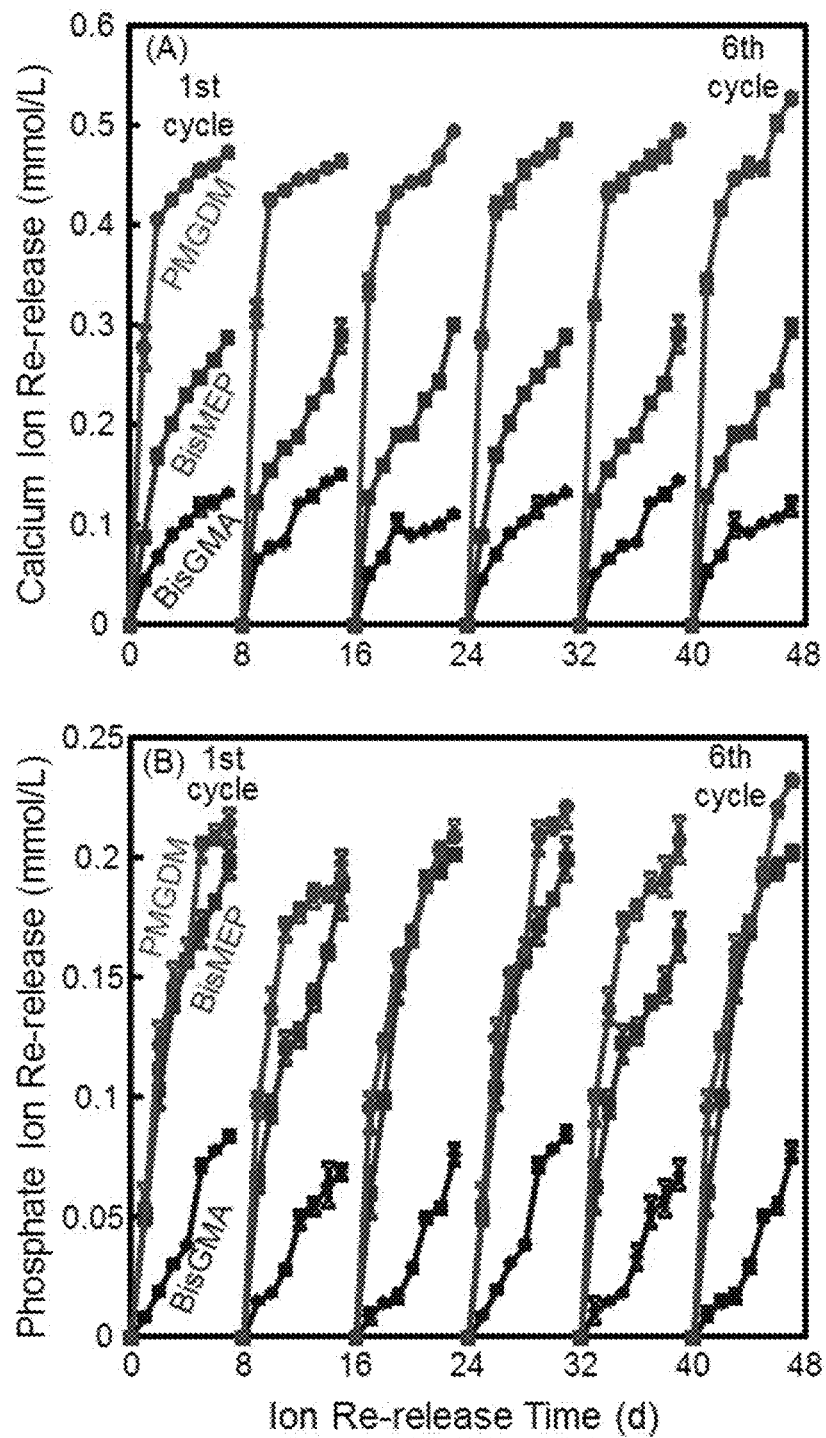
FIGS. 4A-4B. NACP nanocomposites first had ion release for 70 d to exhaust the ion release, then were recharged and their Ca ion (FIG. 4A) and P ion (FIG. 4B) re-release was measured (mean±sd; n=3). Six cycles of recharge/re-release were tested for the three NACP nanocomposites.

The NACP nanocomposites without further ion release (after 70 d) were recharged and their ion re-release was measured; the results are plotted in FIG. 4. Each value is mean±sd, with n=3. Specimens were immersed in fresh solution at pH 4 and the re-release was measured for 7 d, as one cycle. Six recharge/re-release cycles were included in FIG. 4. For Ca ion re-release (FIG. 4A), the NACP nanocomposite in PMGDM group had the greatest re-release, followed by BisMEP group (p<0.05). The BisGMA group had the least re-release (p<0.05). For P ion re-release (FIG. 4B), PMGDM and BisMEP groups had similarly high releases, while the BisGMA group had the lowest re-release (p<0.05). Their re-release reached similar ion concentration levels for each cycle, showing that the ion re-release from these NACP nanocomposites was maintained with no decrease from cycle 1 to cycle 6.

Figures 5A, 5B:
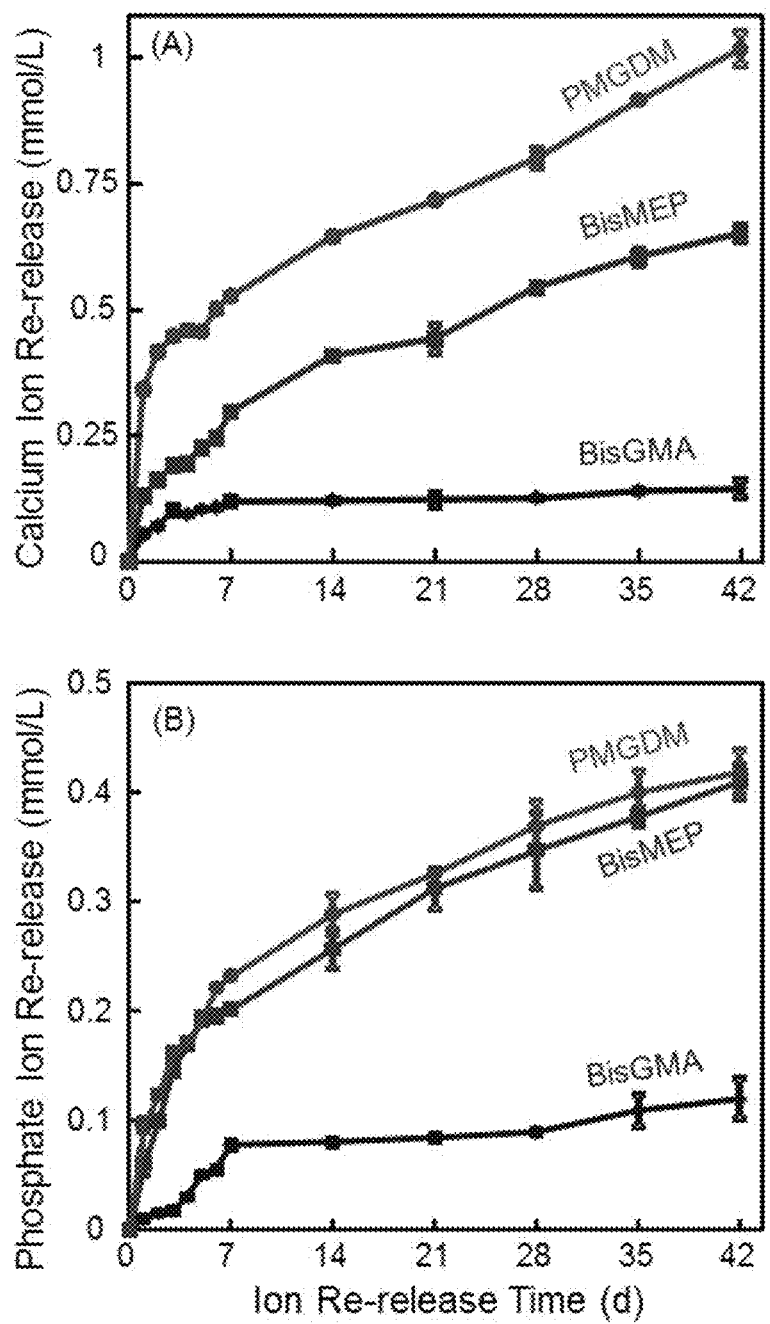
FIGS. 5A-5B. NACP nanocomposites after six recharge/re-release cycles were then tested for continuous Ca ion (FIG. 5A) and P ion (FIG. 5B) release without further recharge (mean±sd; n=3). NACP nanocomposites with acidic monomers PMGDM and BisMEP had greater re-release than BisGMA group (p<0.05). PMGDM group had the greatest Ca ion release (p<0.05). PMGDM and BisMEP groups had similarly high P ion release (p>0.1).

After 6 recharge/re-release cycles, the NACP nanocomposite specimens were used, without further recharge, to measure continuous Ca and P ion release for 42 d, with results in FIG. 5. NACP nanocomposite for the PMGDM and BisMEP groups had greater ion release than the BisGMA group (p<0.05). PMGDM group had the highest level of Ca ion release (FIG. 5A) (p<0.05), while PMGDM and BisMEP groups had similarly high levels of P ion release (FIG. 5B) (p>0.1). These results showed that after the recharge and re-release cycles in FIG. 4, the NACP nanocomposite specimens could continue the re-release for a relatively long period of time.

Thus, rechargeable CaP dental composites were developed for the first time, demonstrating successful recharge and prolonged re-release of Ca and P ions. The NACP nanocomposite using the PMGDM-EBPAGMA resin showed the best recharge/re-release capability. PMGDM is an acidic adhesive monomer that was previously used in dental bonding agent and in a CaP-based cement [29,30].

Due to its active carboxylate group, it can chemically chelate with calcium or phosphate ions of dentin or of the exterior environment such as a recharging composition.

Four points should be noted for the NACP nanocomposite in the PMGDM group of the present study. (1) After recharge, the re-releasing effect detected in the PMGDM composite lasted for at least 7 d (FIG. 4). (2) After repeated recharge/re-release cycles, the extent of Ca and P ion re-release showed no trend of decrease with increasing the number of cycles, which indicated a long-term caries-inhibition potential and could be highly beneficial clinically. (3) After the 6th cycle of recharge and the specimens were re-released for 7 d, the specimens without further recharge could continue the re-release for at least another 42 d (FIG. 5). (4) The specimens were immersed in a pH 4 solution to measure the ion release in the present study as an accelerated experiment. In the oral environment, acidogenic bacteria ferment carbohydrates and produce organic acids including lactic, formic, acetic, and propionic acids [31]. As a result, the oral plaque pH after a sucrose rinse can decrease to 4.5 or even 4 [32]. The Stephan Curve shows that the plaque pH, following a glucose mouthrinse, stays in the cariogenic area for about 30 min, and then increases back to a safe pH of 5.5 or higher, after the bacteria have completed their metabolization of the glucose and the saliva has buffered the acid [32]. Therefore, the low pH environment in vivo would last only about 30 min after a glucose rinse or a meal. This would account for only a couple of hours of accumulated low pH time per day in vivo. This time is a much shorter than the 24 h immersion/day in pH 4 solution in the experiments which could exhaust the ion release much faster from the composite. Therefore, after the recharge, the re-release of Ca and P ions from the NACP nanocomposite in the PMGDM group could potentially last much longer than 42 d in vivo with only intermittent acid attacks. It is possible that the patients could potentially use the recharging composition, for example a mouthrinse, three times per day for three days to recharge the NACP nanocomposite, and then the re-release could last for several months before another recharge would be needed.

Example 2

NACP-Containing Adhesive Fabrication

NACP [$Ca_3(PO_4)_2$] were synthesized via a spray-drying technique as previously described [13,16]. Briefly, calcium carbonate and dicalcium phosphate anhydrous were dissolved into an acetic acid solution. The concentrations of Ca and P ion concentrations were 8 mmol/L and 5.333 mmol/L, respectively, yielding a Ca/P molar ratio of 1.5. The solution was sprayed into a heated chamber to evaporate the water and volatile acid. The dried NACP powder was collected by an electrostatic precipitator. Previously studies showed that the NACP mean particle size was approximately 116 nm [13,16].

Three experimental bonding agents were investigated. A pyromellitic glycerol dimethacrylate (PMGDM) containing primer, previously reported to yield good dentin bonding properties, was adopted as the primer for all three groups in the present study [33]. This primer contained PMGDM (Hampford, Stratford, Conn.) and 2-hydroxyethyl methacrylate (HEMA) (Esstech, Essington, Pa.) at a mass ratio 3.3/1, with 50% acetone solvent (all mass fractions) [37].

Three adhesives were formulated (Table 3). The first consisted of PMGDM and ethoxylated bisphenol A dimethacrylate (EBPADMA) (Sigma-Aldrich, St, Louis, Mo.) at 1:1 mass ratio, which was rendered light-curable with 1% phenylbis (2,4,6-trimethylbenzoyl) phosphine oxide (Esstech) [34,36]. A preliminary study showed a high level of Ca and P ion release and recharge using the PMGDM-EBPADMA resin. PMGDM is an acidic adhesive monomer [42,43] and can chelate with calcium ions from the recharging solution to achieve the recharging capability. The PMGDM-EBPADMA group is referred to as adhesive PE.

To make the second adhesive, 10% of HEMA was added to the PMGDM and EBPADMA mixture to improve flowability and hydrophilicity, following a previous study [34]. This group is denoted adhesive PEH as listed in Table 3. The third adhesive incorporated 10% HEMA and 5% bisphenol A glycidyl dimethacrylate (BisGMA) (Esstech) into the PMGDM-EBPADMA adhesive. Previous studies showed that a small amount of BisGMA could improve the cross-linkage of monomers and the bonding properties of the adhesive [35,44]. This adhesive is designated PEHB.

TABLE 3

Compositions (mass %) of experimental adhesives of the present study

| Adhesive | PMGDM | EBPADMA | HEMA | Bis-GMA | BAPO |
|---|---|---|---|---|---|
| PE | 49.5 | 49.5 | — | — | 1 |
| PEH | 44.5 | 44.5 | 10 | — | 1 |
| PEHB | 44.5 | 39.5 | 10 | 5 | 1 |

PMGDM: pyromellitic glycerol dimethacrylate (Hampford, Stratford, CT).
EBPADMA: ethoxylated bisphenol A dimethacrylate (Sigma-Aldrich, St, Louis, MO).
Bis-GMA: bisphenol A glycidyl dimethacrylate (Esstech, Essington, PA).
HEMA: 2-hydroxyethyl methacrylate (Esstech, Essington, PA).
BAPO: phenylbis (2,4,6-trimethylbenzoyl) phosphine oxide (Esstech, Essington, PA).

NACP fillers were mixed into each adhesive at mass fractions of 0%, 20% and 30%, following previous studies [37,38]. NACP filler levels ≥40% were not used due to slightly reduced dentin bond strength in preliminary study. Hence, nine adhesives were fabricated: (1) Adhesive PE+0% NACP; (2) Adhesive PE+20% NACP; (3) Adhesive PE+30% NACP; (4) Adhesive PEH+0% NACP; (5) Adhesive PEH+20% NACP; (6) Adhesive PEH+30% NACP; (7) Adhesive PEHB+0% NACP; (8) Adhesive PEHB+20% NACP; (9) Adhesive PEHB+30% NACP.

Dentin Shear Bond Strength Testing

Extracted human third molars were collected and stored in 0.01% thymol solution at 4° C. and used within 1 month after extraction. Each tooth was sectioned perpendicularly to the axis of the tooth to expose the mid-coronal dentin surface using a low speed diamond saw (Isomet, Buehler, Lake Bluff, Ill.) under water coolant. Dentin surfaces were polished with 600-grit SiC paper. Then the dentin surface was etched with 37% phosphoric acid gel for 15 seconds (s) and rinsed with water. Two coats of the primer were applied on the etched dentin with a brush-tipped applicator for 15 s. The dentin was gently blown with air for 5 s. An adhesive was then applied and light-cured for 10 s with an Optilux curing unit (VCL 401, Demeron Kerr, Danbury, Conn.). A stainless-steel cylindrical mold (inner diameter=4 mm, thickness=1.5 mm) was placed on the adhesive-treated dentin surface. A composite (TPH, Caulk/Dentsply, Milford, Del.) was filled into the mold and light-cured for 60 s. The bonded specimens were stored in distilled water at 37° C. for 24 hours (h). A chisel on a Universal Testing Machine (MTS, Eden Prairie, Minn.) was aligned to be parallel to the composite-dentin interface [37,38]. Load was applied at a cross-head of 0.5 mm/min until the bond failed. Dentin shear bond strength=$4P/(\pi d^2)$, where P is the load at failure, and d is the diameter of the composite [37,38].

Ca and P Ion Release Measurement

A sodium chloride (NaCl) solution (133 mmol/L) was buffered to pH 4 with 50 mmol/L lactic acid to measure ion release, simulating a cariogenic low pH condition [38,41]. For each NACP-adhesive group, three specimens with size of approximately 2×2×12 mm were immersed in 50 mL of solution to yield a specimen volume/solution of 2.9 mm$^3$/mL. This was similar to a specimen volume per solution of about 3.0 mm$^3$/mL in a previous study [39]. The Ca and P ion concentrations released from the specimens were measured at 1, 3, 5, 7, 14, 21, 28, 35, and 42 days (d). At each time, aliquots of 0.5 mL were removed and replaced with fresh solution. The pH of the immersion solutions was monitored and adjusted to pH 4 with 50 mmol/L lactic acid using a combination pH electrode (Orion, Cambridge, Mass.) [45]. The aliquots were analyzed for Ca and P concentrations via a spectrophotometric method (DMS-80 UV-visible, Varian, Palo Alto, Calif.) using known standards and calibration curves [38,41]. Six batches of specimens were tested and the ion release values were averaged for each adhesive. This virgin ion release from the adhesive specimens was termed "initial release", to differentiate from the subsequent recharge and re-release.

Recharge of Adhesive Specimens and Re-Release of Ca and P Ions

Figure 6:
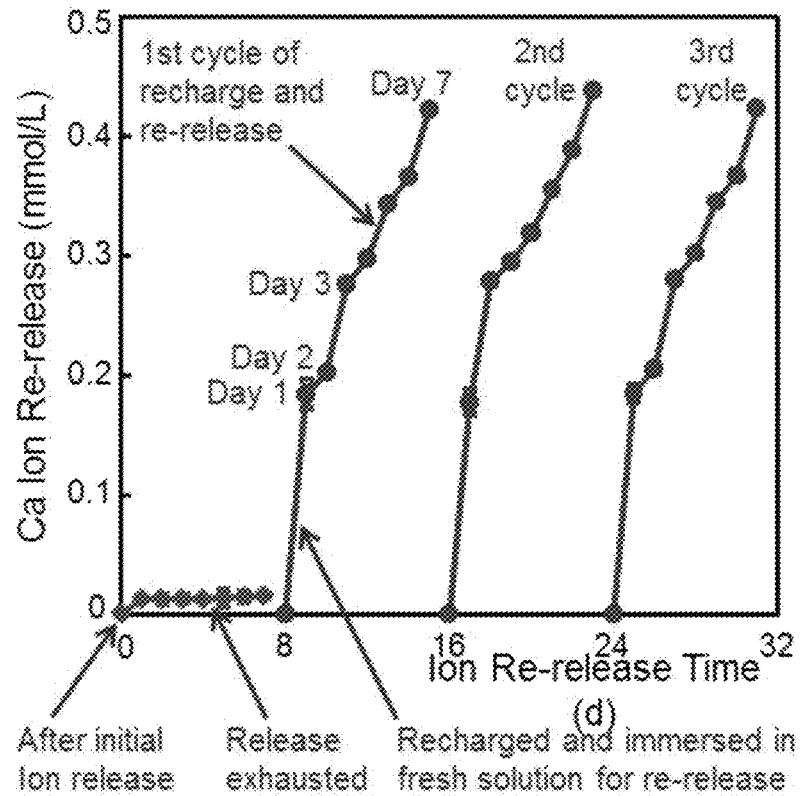
FIG. 6. Illustration of Ca and P ion recharge and re-release testing method. Adhesive specimens were first immersed in a pH 4 solution to exhaust the ion release, as indicated by the lower left arrow. Then the specimens were immersed in a new pH 4 solution to confirm that the ion release was exhausted, as indicated by the lower middle arrow. The exhausted specimens were recharged in a recharge solution. The specimens were then tested for Ca and P ion re-release for 7 d, as indicated by the third arrow at the bottom of FIG. 6. This constituted the first recharge/re-release cycle. This process was repeated for 3 cycles to test whether the recharge/re-release capability would decrease over time.

The procedures of recharge and re-release are illustrated in FIG. 6. Specimens were immersed in the pH 4 solution for 42 d to measure the initial ion release as described above. After 42 d immersion, the specimens were collected and stored in 100 mL of fresh NaCl solution at pH 4 for 30 d to exhaust their ion release. The immersion solution was refreshed daily to promote the release of Ca and P ions. Then the specimens were removed from the immersion solution and ultrasonicated with distilled water for 30 min. Then, these exhausted specimens were used for Ca and P ion measurement for 7 d to confirm that their ion release was exhausted and there was no further release, as indicated by the two arrows at the lower left corner in FIG. 6.

The exhausted specimens were then used for the recharge experiment. The calcium ion recharge solution consisted of 100 mmol/L of $CaCl_2$ and 50 mmol/L of 4-(2-hydroxyethyl)-1-piperazineethanesulfonic acid (HEPES) buffer [40,46]. The phosphate ion recharge solution consisted of 60 mmol/L of $KHPO_4$ and 50 mmol/L of HEPES. The two solutions were adjusted to pH 7 using 1 mol/L of KOH [40,46]. To recharge, three specimens of 2×2×12 mm were immersed into 5 mL of the Ca or P recharge solution and gently shaken on a mixing machine (Analog Vortex Mixer, Fisher, Waltham, Mass.) at a power level of 3 for 3 min. This immersion and shaking treatment simulated the movement in the mouth-rinsing process. Then the specimens were rinsed with running distilled water for 1 min to remove any loosely attached deposits on specimen surfaces (hence only the ions recharged into the interior of the resin were measured in the subsequent re-release test). This recharge was performed at about 9:00 am, then the specimens were kept in lab air, and then they were recharged again at about 5:00 pm. Thus the specimens received two doses of recharge, simulating a mouth-rinse in the morning and in the evening. Then the specimens were used to measure the re-release.

To measure Ca and P ion re-release, the recharged specimens were immersed in 50 mL of the pH 4 solution as described above, as indicated by the third arrow in the bottom of FIG. 6. To test the recharge/re-release cycle repeatedly for several cycles to investigate the durability, each cycle of re-release measurement lasted for 7 d (the upper arrow in FIG. 6 indicates the measurement from 1 d to 7 d in the first cycle). After 7 d of re-release, the specimens were recharged again as described above, and tested for re-release as cycle 2. This was repeated for 3 cycles in the present study as illustrated in FIG. 6.

After 3 cycles of recharge/re-release, in order to investigate how long the specimens could further release Ca and P ions, the specimens after the 3rd cycle (without further recharge) were immersed in 50 mL of fresh pH 4 solution to measure ion release. The measurements of Ca and P ion re-release from these specimens were continued for an additional 42 d. The concentrations of Ca and P ions were measured at 1, 2, 3, 4, 5, 6, 7, 14, 21, 28, 35 and 42 d. For each adhesive, three batches of specimens were tested and the values were averaged for the ion re-release [38,41].

Statistical Analysis

Kolmogorov-Smirn test and Levene test were performed to confirm the normality and equal variance of data. The results of shear bond strength and Ca and P ion release were analyzed with two-way analyses of variance (ANOVA). Post hoc multiple comparisons were performed using the Tukey's honestly significant difference test. Statistical significance was set at $p<0.05$, using the SPSS 14.0 software package (SPSS, Chicago, Ill., USA).

Results

Figure 7:
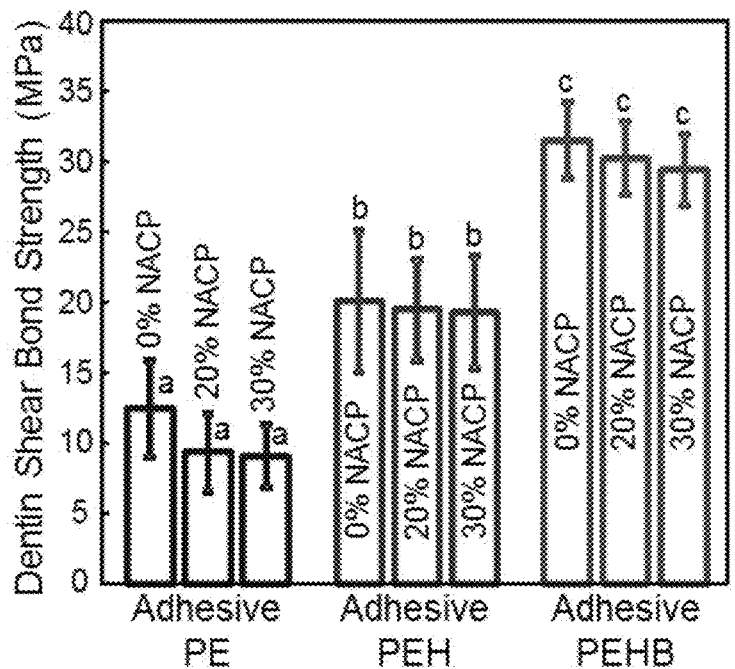
FIG. 7. Dentin shear bond strength tested after storage in water for 24 hours (hereinafter hours is abbreviated as "h") using extracted human teeth (mean±sd; n=10). Bars with dissimilar letters indicate values that are significantly different from each other (p<0.05).

Dentin shear bond strength results are plotted in FIG. 7 (mean±sd, n=10). The different adhesive types had a significant effect on dentin bond strength ($p<0.05$). Adhesive PEHB had the highest dentin bond strength followed by PEH, while PE had the lowest bond strength ($p<0.05$). For each adhesive type, the NACP filler level of 0-30% had no significant effect on dentin bond strength ($p>0.1$).

Figures 8A, 8B, 8C, 8D, 8E, 8F:
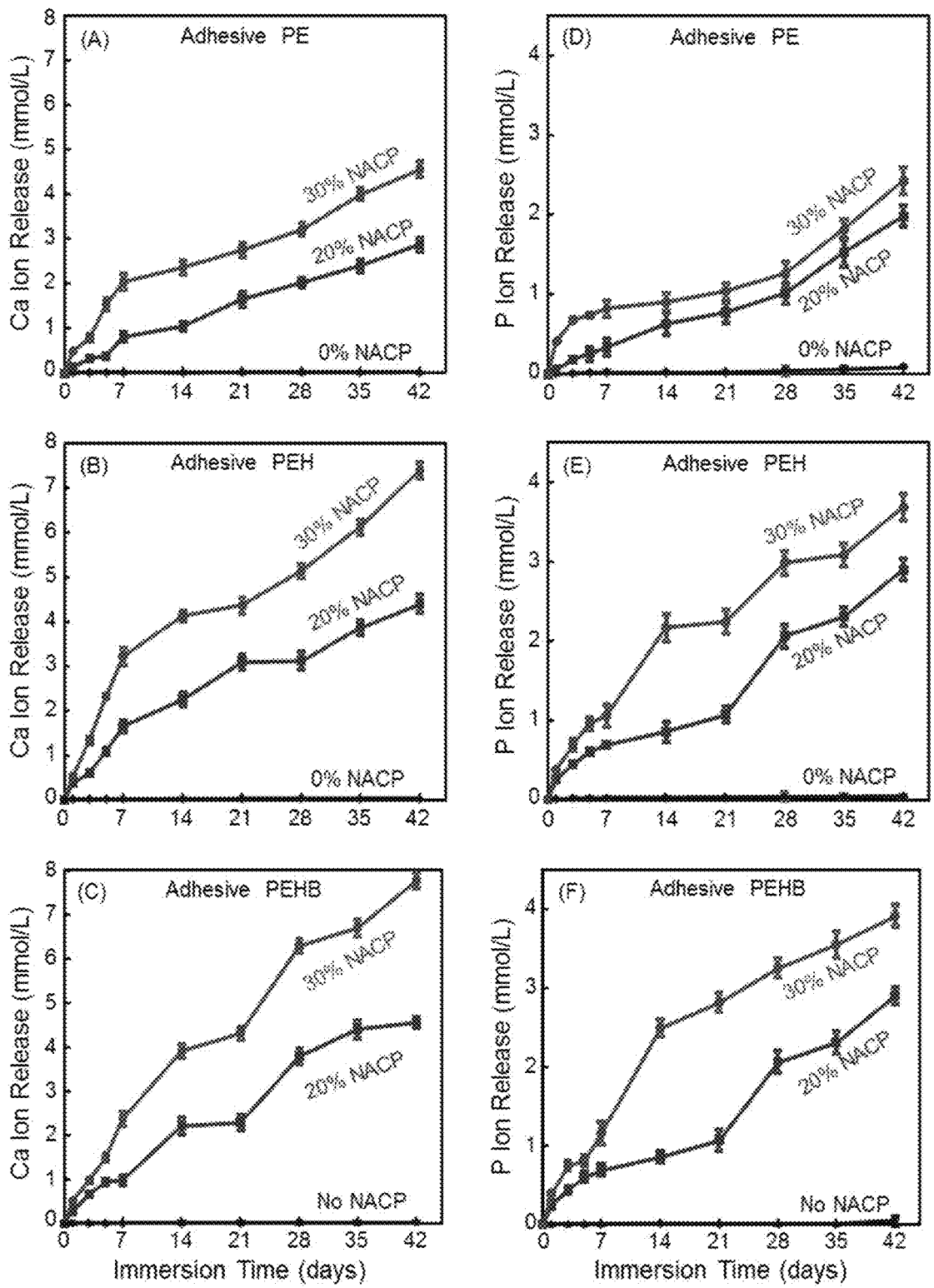
FIGS. 8A-8F. Initial Ca and P ion release (mean±sd; n=6) from the adhesive specimens. Ca and P ion release of adhesive PEH (FIG. 8B, 8E) and adhesive PEHB (FIG. 8C, 8F) were significantly higher than that of adhesive PE (FIG. 8A, 8D) with the same NACP content (p<0.05). Increasing the NACP content increased the Ca and P ion release (p<0.05)

The initial Ca and P ion release from the virgin adhesive specimens are plotted in FIG. 8 (mean±sd; n=6). There was no Ca and P release at 0% NACP. The release significantly increased when the NACP filler level was increased from 20% to 30% ($p<0.05$). PEHB had the most ion release (FIGS. 8C, 8F), followed by PEH (FIGS. 8B, 8E) ($p<0.05$). PE had the least ion release (FIGS. 8A, 8D). For all NACP-containing adhesives, the ion concentrations significantly increased with time from 1 to 42 d ($p<0.05$).

Figures 9A, 9B, 9C, 9D, 9E, 9F:
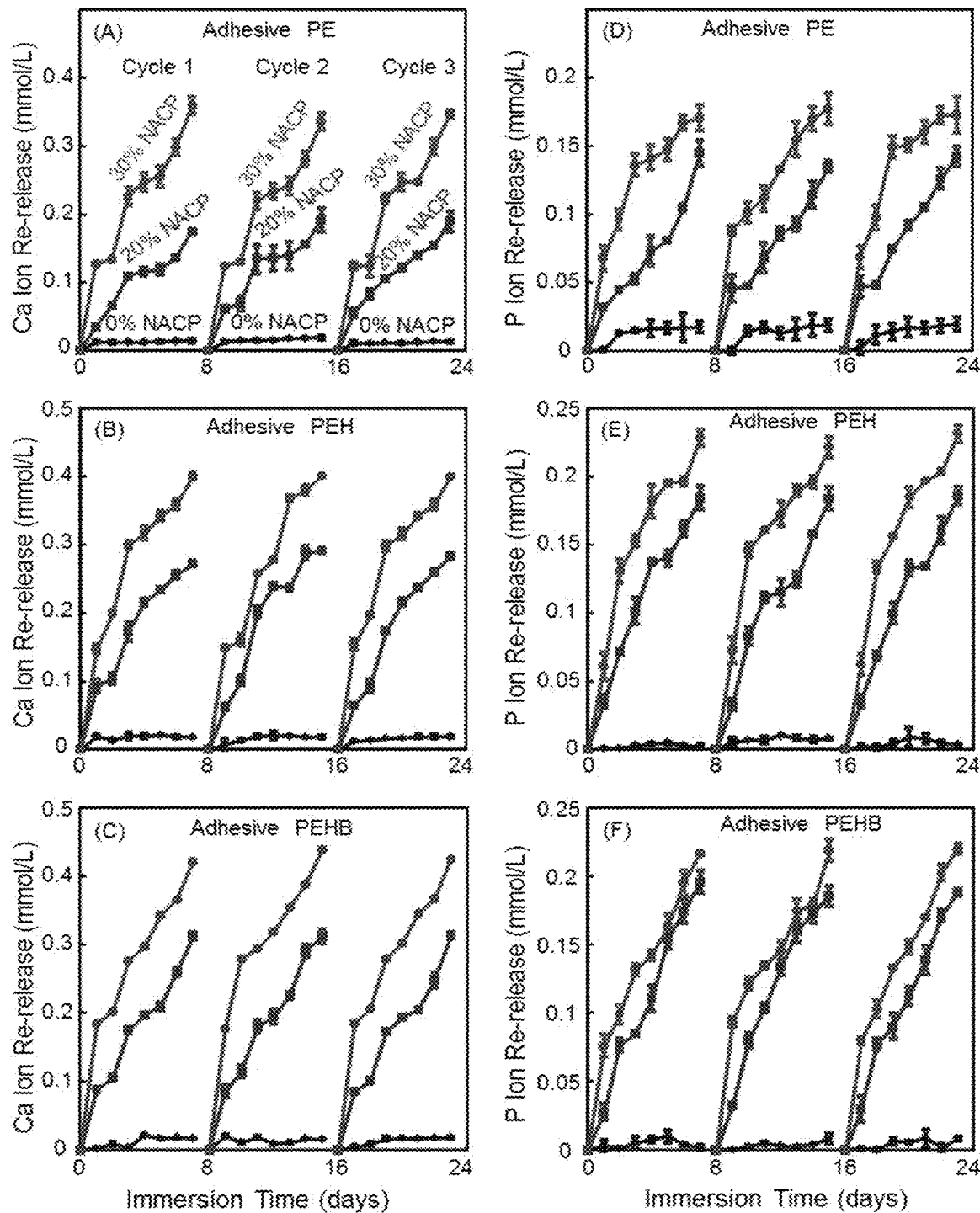
FIGS. 9A-9F. Ca and P ion re-release after recharge (mean±sd; n=3). Ca and P ion re-release of adhesive PEH (FIG. 9B, 9E) and adhesive PEHB (FIG. 9C, 9F) were significantly higher than that of adhesive PE (FIG. 9A, 9D) with the same NACP content (p<0.05). There was no decrease in the re-release level with increasing the recharge/re-release cycle from cycle 1 to 3 (p>0.1).

The Ca and P ion recharge and re-release results are plotted in FIG. 9 (mean±sd, n=3). The exhausted specimens were recharged and the ion re-release was measured for 7 d, as one cycle. Three recharge/re-release cycles were plotted in FIG. 4. Adhesives without NACP showed little re-release after each recharge. For each adhesive, increasing the NACP filler level to 20% and 30% greatly increased the ion re-release ($p<0.05$). For each adhesive, there was no decrease in ion release from the first recharge/re-release cycle to the third cycle. For each cycle, the ion release reached a similarly high level, demonstrating a long-term recharge/re-release capability. Comparing the three types of adhesives, PEHB had the best recharge and re-release capability (FIGS. 9C, 9F), followed by PEH (FIGS. 9B, 9E) and then PE (FIGS. 9A, 9D).

Figures 10A, 10B, 10C, 10D, 10E, 10F:
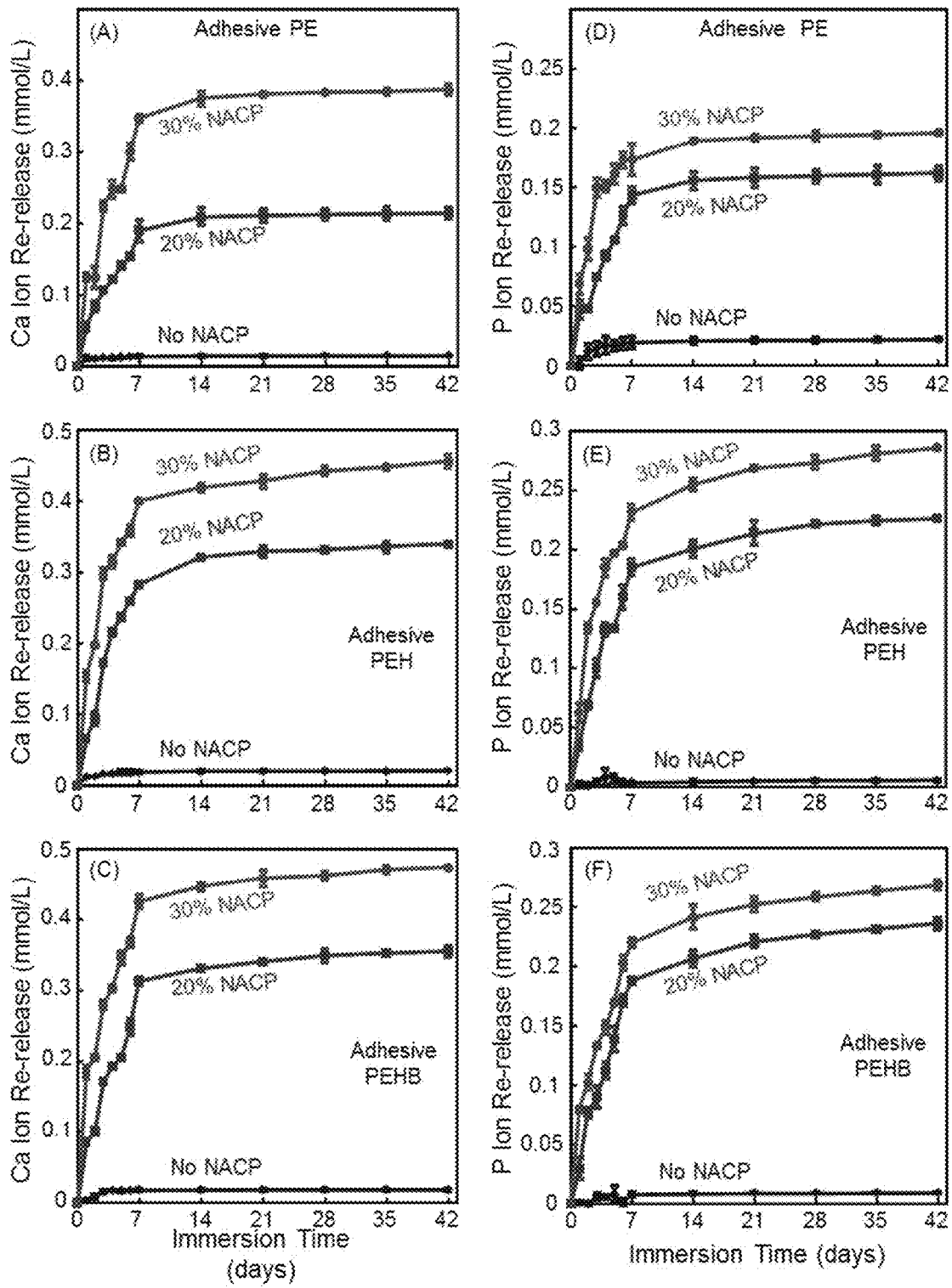
FIGS. 10A-10F. After the third recharge/re-release cycle with ion release for 7 d (after FIG. 4), the specimens without further recharge were tested for continuous Ca and P ion release for 42 d (mean±sd; n=3). Adhesive PEH (FIG. 10B, 10E) and PEHB (FIG. 10C, 10F) had greater re-release than adhesive PE (FIG. 10A, 10D) (p<0.05). The ion concentration increased for about two weeks and then gradually showed plateauing. Therefore, the recharged specimens (without further recharge) could re-release ions for 7 d in FIG. 4 and then two more weeks in FIG. 5.

After the third recharge/re-release cycle, the continuous Ca and P ion re-release of the specimens without further recharge was measured for 42 d (FIG. 10) (mean±sd, n=3). For NACP-containing adhesives, adhesive PEH (FIGS. 10B, 10E) and PEHB (FIGS. 10C, 10F) had higher Ca and P ion re-release than adhesive PE (FIGS. 10A, 10D) ($p<0.05$). Adhesive PEH and PEHB had similar ion release levels ($p>0.1$). The release was higher at higher NACP filler level ($p<0.05$). The released ion concentrations significantly increased from 1 d to about 14 d and then gradually reached a plateau. These results demonstrate that after the third recharge, the specimens released Ca and P ions for 7 d in FIG. 4 and then 14 d in FIG. 10, hence they could release ions for a total of 21 d after the recharge.

These results show that a calcium phosphate ion rechargeable bonding agent was developed and the effects of resin composition and NACP filler level on dentin bond strength and CaP recharge and re-release were determined for the first time. Among the three adhesives tested, the adhesive PEHB with 30% NACP showed the highest initial Ca and P ion release, the greatest recharge and re-release capability, as well as the highest dentin bond strength compared to PEH and PE. Adhesive PEHB showed the highest dentin bond strength, and increasing the NACP content from 0% to 30% did not compromise the dentin bond strength. PEHB had the highest initial Ca and P ion release, followed by PEH and PE. PEHB had the greatest Ca and P ion recharge and re-release, followed by PEH and PE. After recharge, the resins had continuous release of ions for at least 2-3 weeks, before another recharge would be needed. For each adhesive, NACP at 30% yielded much better Ca and P release, recharge and re-release than 20% NACP. Among all the bonding agents tested, PEHB with 30% NACP appeared to be the best, considering its highest dentin bond strength, Ca and P ion release, and recharge and re-release.

Example 3

Preparation of NACP Filler Particles

NACP [$Ca_3(PO_4)_2$] was synthesized via a spray-drying technique as previously described [13,16]. Briefly, calcium carbonate and dicalcium phosphate anhydrous were dissolved into an acetic acid solution. The concentrations of Ca and P ions were 8 mmol/L and 5.333 mmol/L, respectively, yielding a Ca/P molar ratio of 1.5. The solution was sprayed into a heated chamber to evaporate the water and volatile acid. The dried NACP powders were collected by an electrostatic precipitator. Previously studies showed the mean size of the NACP was approximately 166 nm [49].

Formulations of the Experimental Orthodontic Cements

A powder/liquid formulation was used in this study to fabricate the orthodontic cements according to the previous study [53]. Two resin matrices were formulated with different resin monomers (Table 4). The first consisted of pyromellitic glycerol dimethacrylate (PMGDM) (Hampford, Stratford, Conn.) and ethoxylated bisphenol A dimethacrylate (EBPADMA) (Sigma-Aldrich, St, Louis, Mo.) at mass ratio of 1:1, according to a CaP remineralization cement in the previous study [53]. Camphorquinone (CQ) (Irgacure819, Ciba Chemicals, Japan) was added to enable a light cure and Benzoyl peroxide (BPO) (Irgacure819, Ciba Chemicals, Japan) was added to enable a chemical cure. The PMGDM-EBPADMA group is referred to as cement PE (Table 4). To make the second resin matrix, 10% of HEMA (Esstech, Essington, Pa.) and 5% of bisphenol A glycidyl dimethacrylate (BisGMA) (Esstech) were added to the PMGDM and EBPADMA mixture. Both HEMA and Bis-GMA are traditional monomers widely used in dental adhesives. HEMA is an excellent adhesion-promoting monomer due to its good biocompatibility and hydrophilicity. Previous studies showed that a small amount of BisGMA could improve the cross-linkage of monomers and the bonding properties of the adhesive [56,57]. A preliminary study showed a significant high bond strength to enamel with the addition of 10% HEMA and 5% BisGMA. The second resin matrix is denoted cement PEHB as listed in Table 4.

TABLE 4

Composition (% by mass) of resin matrices of cements in the study

| Experimental | Liquid | | | | Powder | |
|---|---|---|---|---|---|---|
| cements | PMGDM | EBPADMA | HEMA | Bis-GMA | BPO | CQ |
| PE | 49.5 | 49.5 | — | — | 0.8 | 0.2 |
| PEHB | 44.5 | 39.5 | 10 | 5 | 0.8 | 0.2 |

PMGDM: pyromellitic glycerol dimethacrylate (Hampford, Stratford, CT); EBPADMA: ethoxylated bisphenol A dimethacrylate (Sigma-Aldrich, St, Louis, MO); Bis-GMA: bisphenol A glycidyl dimethacrylate (Esstech, Essington, PA); HEMA: 2-hydroxyethyl methacrylate; CQ: camphorquinone (Irgacure819, Ciba Chemicals, Japan); BPO: benzoyl peroxide (BPO) (Irgacure819, Ciba Chemicals, Japan).

NACP fillers were added into the aforementioned two cements respectively at mass fraction of 40%, following previous studies [49,50]. NACP filler levels >40% were not used due to a decrease in enamel bond strength in preliminary study. Therefore, four cements were fabricated in the present study: (1) Cement PE; (2) Cement PE+40% NACP; (3) Cement PEHB; (4) Cement PEHB+40% NACP. All cements were freshly prepared by hand mixing the all the formulations for 2 minutes (min) before using, according to a previous study [53]. Orthodontic bracket shear bond testing and the adhesive remnant index (ARI).

Four experimental cements and one commercial orthodontic cement Transbond XT (referred as TXT control) (3M Unitek, Monrovia, Calif.) were subjected to the orthodontic bracket shear bond testing, using the method as previously described [58]. Transbond XT consisted of silane treated quartz (70-80% by weight), bisphenol-Adiglycidylether dimethacrylate (10-20%), bisphenol-A-bis (2-hydroxyethyl) dimethacrylate (5-10%), silane-treated silica (<2%) and diphenyliodonium hexafluorophosphate (<0.2%), according the manufacturer. Extracted, intact human third molars were collected and stored in 0.01% thymol solution at 4° C. and used within 1 month (mon) after extraction. Each tooth was embedded vertically in a self-curing acrylic resin (Lang Dental Manufacturing, Wheeling, Ill.) taking into account the buccal axis of the clinical crown, so that their labial surface would be parallel to the force during the shear bond test. The coronal portion was submitted to prophylaxis with oil-free pumice and rubber cups at a low speed for 10 seconds (s). Samples were washed and dried for 15 s. The buccal tooth surfaces were etched with 35% phosphoric acid (Scotchbond, 3 M ESPE, St. Paul, Minn.) for 30 s, then washed and dried until with frosty white appearance. The mixed cement in each group was applied to the base of the bracket, which was placed on the center of the tooth surface with firm pressure. Excessive cement around the bracket was removed. The cement was polymerized from all four sides (mesial, distal, occlusal, and gingival) of the bracket for 10 s each using a light-curing unit (Optilux VCL 401, Demetron Kerr, Danbury, Conn.). The specimens were stored in water at 37° C. for 24 hours (h). A chisel on a Universal Testing Machine (MTS, Eden Prairie, Minn.) was positioned on the upper part of the bracket base and parallel to the resin-enamel interface. An occlusogingival load (1 kN) was applied at a cross-head of 0.5 mm/min until the bracket detached. Orthodontic bracket shear bond strength=load at failure/bracket surface area.

After brackets were detached, each tooth surface was observed under a stereomicroscope (Leica Zoom 2000—Leica Microsystems GmbH—Wetzlar, Germany) to examine the failure mode. The Adhesive Remnant Index (ARI) was scored to assess the remaining cement material on the enamel using the following criteria [58]: 0=no amount of cement remaining in the enamel; 1=less than half of the cement remaining in the enamel; 2=more than half of cement remaining in the enamel; 3=all the cement remaining in the enamel.

Water Sorption Assessment of Experimental Cements

Four NACP containing orthodontic cements were tested for water sorption (WS). Each well-mixed cement paste was placed into a stainless steel mold to prepare resin bars with the size of 2×2×25 mm [48]. The specimen was light-cured (Triad 2000, Dentsply, York, Pa.) for 1 min on each open side of the mold and then incubated at 37° C. for 24 h for a complete polymerization. The bars were then broken in the middle to obtain specimens with size of approximately 2×2×12 mm.

The WS was tested using the method as previously described [59]. The specimens were dried over Drierite desiccants (WA Hammond Drierite, Xenia, Ohio) to constancy until the mass changed less than 0.1 mg. The specimens were then exposed to an air atmosphere of 75% relative humidity at room temperature (23° C.) by keeping them suspended over a saturated aqueous NaCl slurry in closed systems. Gravimetric mass changes were recorded at 3 d, 5 d, 15 d, and 30 d of exposure to this relative humidity. The WS (mass fraction %) of any individual specimen at any given time interval (t) was calculated by relating its mass at the time t, $W_t$, and the mass of a dry specimen ($W_0$; initial dry value) by using the equation: $WS=[(W_t-W_0)/W_0]\times100$. The final WS level of each specimen was presented as the maximum value during the 30 d.

Ca and $PO_4$ Ion Release Measurement

A sodium chloride (NaCl) solution (133 mmol/L) was buffered to pH 4 with 50 mmol/L lactic acid to measure ion release, simulating a cariogenic low pH condition [48, 51]. Three specimens of approximately 2×2×12 mm were immersed in 50 mL of solution to yield a specimen volume/solution of 2.9 $mm^3$/mL. This was similar to a specimen volume per solution of about 3.0 $mm^3$/mL in a previous study [54]. The concentrations of Ca and P released from the specimens were measured at 1 d, 3 d, 5 d, 7 d, 14 d, 21 d, 28 d, 35 d, and 42 d as the method previously described [48,60]. At each time, aliquots of 0.5 mL were removed and replaced by fresh NaCl solution. The pH of the immersion solutions was monitored and adjusted to pH 4 with 50 mmol/L lactic acid using a combination pH electrode (Orion, Cambridge, Mass.) [52]. The aliquots were analyzed for Ca and P concentrations via a spectrophotometric method (DMS-80 UV-visible, Varian, Palo Alto, Calif.) using known standards and calibration curves [48,51]. Six batches of specimens were tested and the ion release values were averaged for each cement. This initial ion release from the cement specimens was termed "virgin release", to differentiate from the subsequent recharge and re-release.

Recharge of Cement Specimens and Ca and P Ions Re-Release

Figure 11:
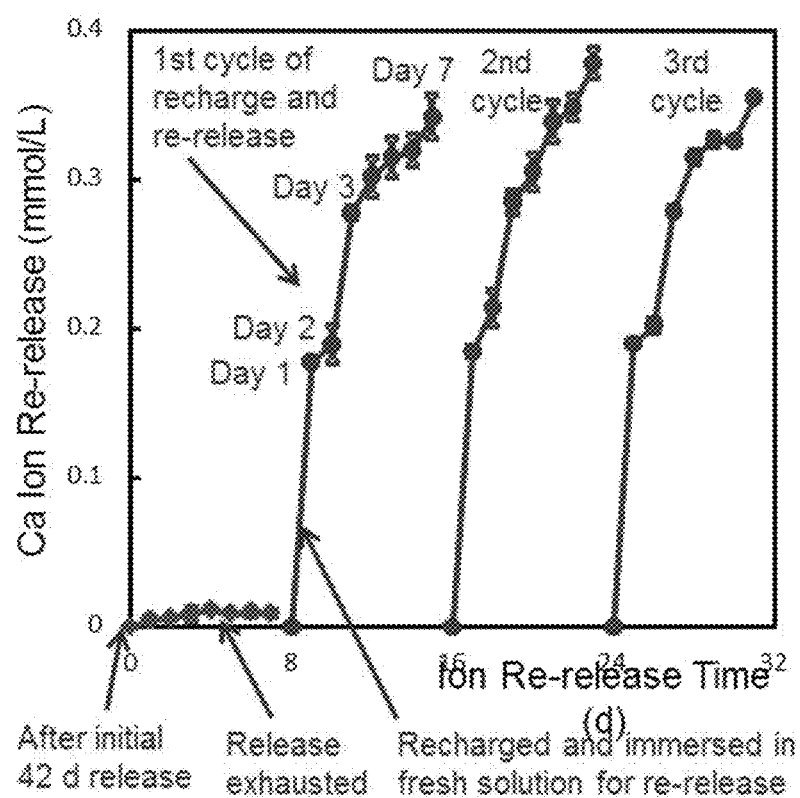
FIG. 11. Illustration of Ca and P ion recharge and re-release testing. Cement specimens were first immersed in a pH 4 solution to exhaust the ion release, as indicated by the lower left arrow. Then the specimens were immersed in a fresh pH 4 solution to confirm that the ion release was exhausted, as indicated by the lower middle arrow. The exhausted specimens were recharged in a Ca or P recharge solution. The specimens were then tested for Ca and P ion re-release for 7 d, as indicated by the third arrow at the bottom of FIG. 11. This process was considered as the first recharge/re-release cycle and noted as cycle 1. This process was repeated for 3 cycles to test whether the recharge/re-release capability would decrease over time.

The procedures of Ca/P ions recharge and re-release are illustrated in FIG. 11. Specimens were immersed in the pH 4 solution for 42 d for measurement of virgin ion release, as described above. The specimens were then collected and stored in 100 mL of fresh pH 4 solution for additional 30 d to exhaust their ion release. The immersion solution was refreshed daily to promote the release of Ca and P ions. After 30 d immersion, the specimens were ultrasonically cleaned with distilled water for 30 min. Then the specimens were subjected to a Ca and P ion release measurement for 7 d to confirm that the ion release was exhausted and there was no further release, as indicated by the two arrows at bottom-left corner in FIG. 11.

The exhausted specimens were then used for Ca/P ion recharge. The calcium ion recharge solution consisted of 100 mmol/L of $CaCl_2$ and 50 mmol/L of 4-(2-hydroxyethyl)-1-piperazineethanesulfonic acid (HEPES) buffer [55,61]. The phosphate ion recharge solution consisted of 60 mmol/L of $KHPO_4$ and 50 mmol/L of HEPES. The two solutions were adjusted to pH 7 using 1 mol/L of KOH [55,61]. Three specimens of approximately 2×2×12 mm were immersed into 5 mL of the Ca or P recharge solution and gently shaken using a mix machine (Analog Vortex Mixer, Fisher Scientific, Waltham, Mass.) at a power level of 3 for 3 min. This process simulated the movement of mouth-rinsing. Then the specimens were rinsed with running distilled water for 1 min to remove any loosely attached deposits on specimen surfaces (hence only the ions recharged into the interior of the resin were measured in the subsequent re-release test). The specimens received two doses of the recharging composition, one at about 9:00 am, and the other at about 5:00 pm, which simulated a mouth-rinse in the morning and in the evening.

After recharging, the specimens were immersed in 50 mL of pH 4 solution to measure the Ca and P ions re-release using the same method described above, as indicated by the third arrow in the bottom of FIG. 11. To test the recharge/re-release cycle repeatedly for several cycles to investigate the durability, each cycle of re-release measurement lasted for 7 d (the upper arrow in FIG. 11 indicates the measurement from 1 d to 7 d in the first cycle). After 7 d of re-release, the specimens were recharged again as described above, and tested for re-release as cycle 2. This was repeated for 3 cycles in the present study as illustrated in FIG. 11.

In order to investigate how long the specimens could further release Ca and P ions after 3 cycles of recharge/re-release, the specimens after 3rd recharge (without further recharge) were immersed in 50 mL of fresh pH 4 solution for additional 42 d. The concentration of Ca and P ion re-released from these specimens were measured at 1, 2, 3, 4, 5, 6, 7, 14, 21, 28, 35 and 42 d. For each cement, three batches of specimens were tested and the values were averaged for the ion re-release [48,51].

Statistical Analysis

Kolmogorov-Smirn test and Levene test were first performed to confirm the normality and equal variance assumptions of the data were not violated. The results of bracket shear bond strength, water sorption, and Ca/P ion release and re-release values were then analyzed with two-way analyses of variance (ANOVA). Post hoc multiple comparisons were performed using the Tukey's honestly significant difference test. The results of ARI were evaluated using the Chi-Square test. Statistical significances in all tests were preset at $p<0.05$, using the SPSS 14.0 software package (SPSS, Chicago, Ill., USA).

Results

Figures 12A, 12B:
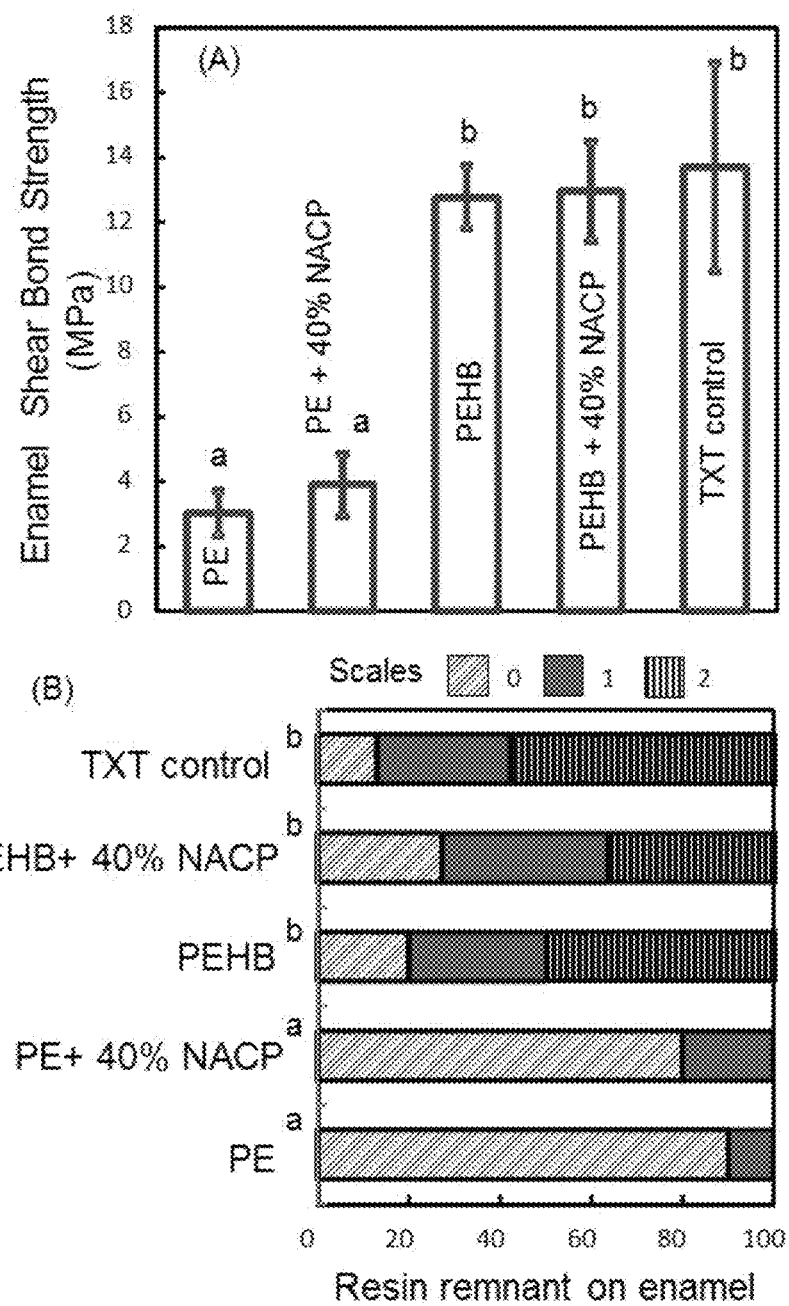
FIGS. 12A-12B. Results for orthodontic bracket shear bond testing.

The orthodontic bracket shear bond strength and ARI results are plotted in FIG. 12. The cement type showed a significant effect on the shear bond strength (FIG. 12A) ($p<0.05$). PEHB and PEHB+40% NACP showed significantly higher shear bond strength than those of PE and PE+40% NACP ($p<0.05$). The incorporation of 40% NACP into the cement showed no effect on the shear bond strength regardless of the cement type ($p>0.1$). Chi-Square test showed significant differences in ARI within cements ($p<0.05$). The ARI scales in groups PEHB and PEHB+40% NACP were significantly higher than those in groups PE and PE+40% NACP (FIG. 12B) ($p<0.05$), which indicated more cements remained on the enamel surfaces in groups PEHB and PEHB+40% NACP after the brackets detached during testing. There was no significant difference in both orthodontic bracket shear bond strength and ARI between PEHB cements and TXT control ($p>0.1$).

Comparisons of the maximum levels of WS during the 30 d are presented in Table 5 (mean±sd; n=6). Both resin matrix type and NACP content showed a significant effect on the WS of the experimental cements ($p<0.05$). PEHB groups showed significantly higher WS value than those of PE groups ($p<0.05$). For both PE and PEHB, the incorporation of 40% NACP significantly increased the WS values ($p<0.05$).

TABLE 5

Water sorption of experimental cements tested in the study [Mean(SD)]

| Cement | NACP Content(mass ratio) | |
|---|---|---|
| | 0% | 40% |
| PE | 0.019 (0.006) $^A$ | 0.023 (0.021) $^{AB}$ |
| PEHB | 0.035 (0.017) $^C$ | 0.072 (0.017) $^D$ |

N = 6 per group. For each horizontal row, values with same letters indicate no significant difference (P > 0.1). For each vertical column, values with same numbers indicate no significant difference (P > 0.1).

Figure 13A:
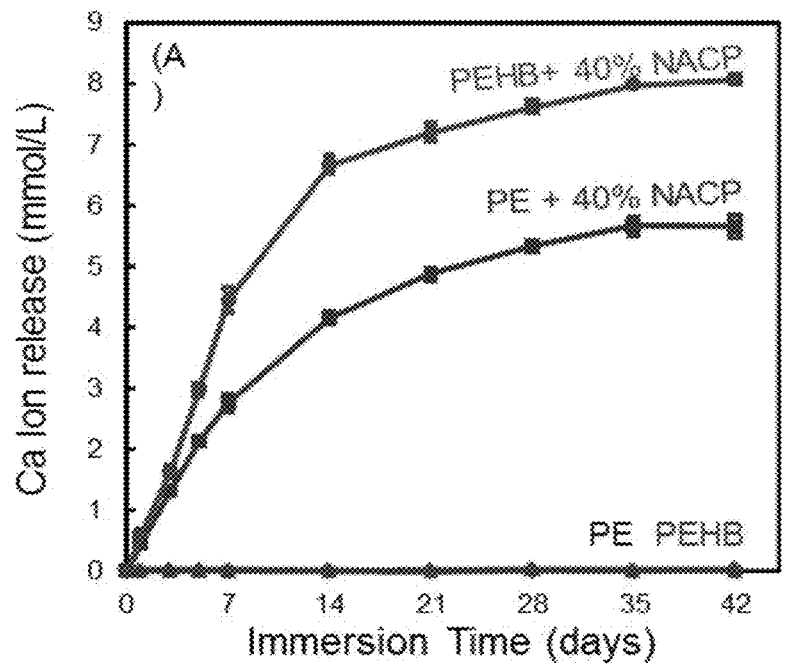
FIGS. 13A-13B. Initial Ca and $PO_4$ ion release (mean±sd; n=6) from the orthodontic cements.
Figure 13B:
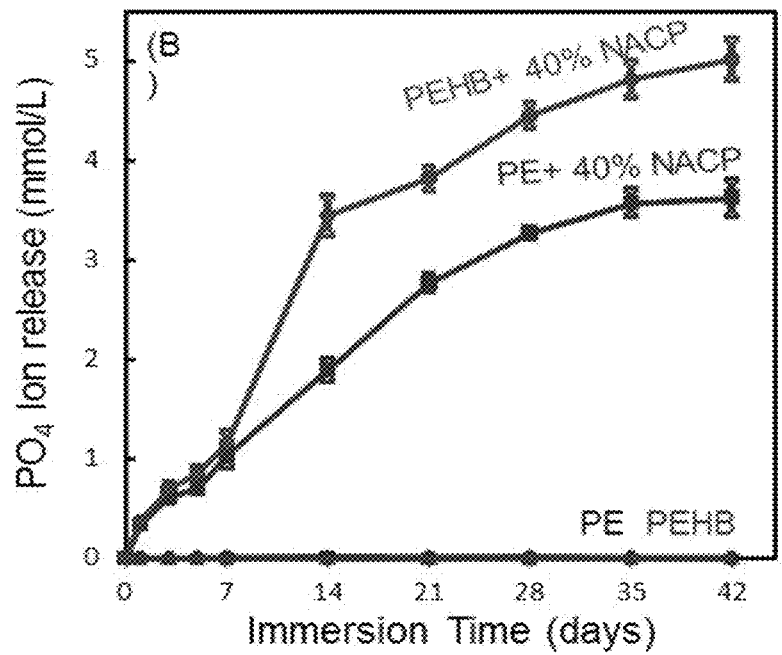

The virgin Ca and $PO_4$ ion release from the cements are plotted in FIG. 13 (mean±sd; n=6). Cements PE and PEHB containing 0% NACP showed the slight levels of Ca (FIG. 13A) and $PO_4$ (FIG. 13B) release near to 0. With incorporation of 40% NACP, both PE+40% NACP and PEHB+40% NACP showed the significantly increased Ca and P ions release ($p<0.05$); and the ion concentrations significantly increased with time from 1 to 42 d ($p<0.05$). The virgin Ca and P ions release of PEHB+40% NACP were significantly higher than those of PE+40% NACP ($p<0.05$).

Figures 14A, 14B:
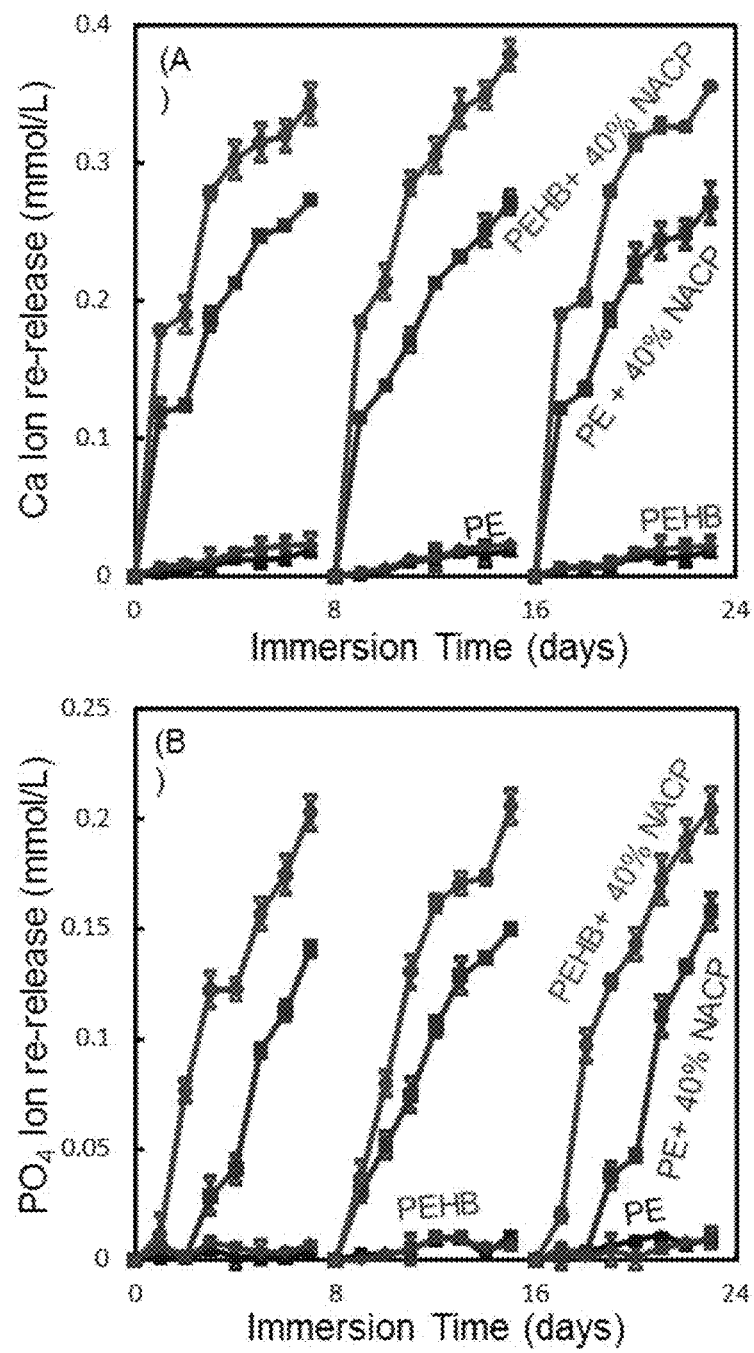
FIGS. 14A-14B. Ca and $PO_4$ ion re-release after recharging (mean±sd; n=3).

The Ca and $PO_4$ ion recharge and re-release profile are plotted in FIG. 14 (mean±sd, n=3). After virgin Ca and P ion release being exhausted, the specimens were recharged and the ion re-re-lease were tested for 7 d, which was noted as one cycle in FIG. 11. Three recharge/re-release cycles were plotted in FIG. 14. Cements without NACP (PE and PEHB) showed little Ca (FIG. 14A) and P ion (FIG. 14B) re-release after each recharge. Both PE+40% NACP and PEHB+40% NACP showed high levels of Ca and P ion re-release after each recharge, which increased from 1 d to 7 d. For each NACP containing cement, there was no decrease in ion re-release from the first recharge/re-release cycle to the third cycle. For each cycle, the ion release reached a similar and high level, demonstrating a long-term recharge/re-release capability. PEHB+40% NACP showed a higher recharge and re-release capability than that of PE+40% NACP.

Figures 15A, 15B:
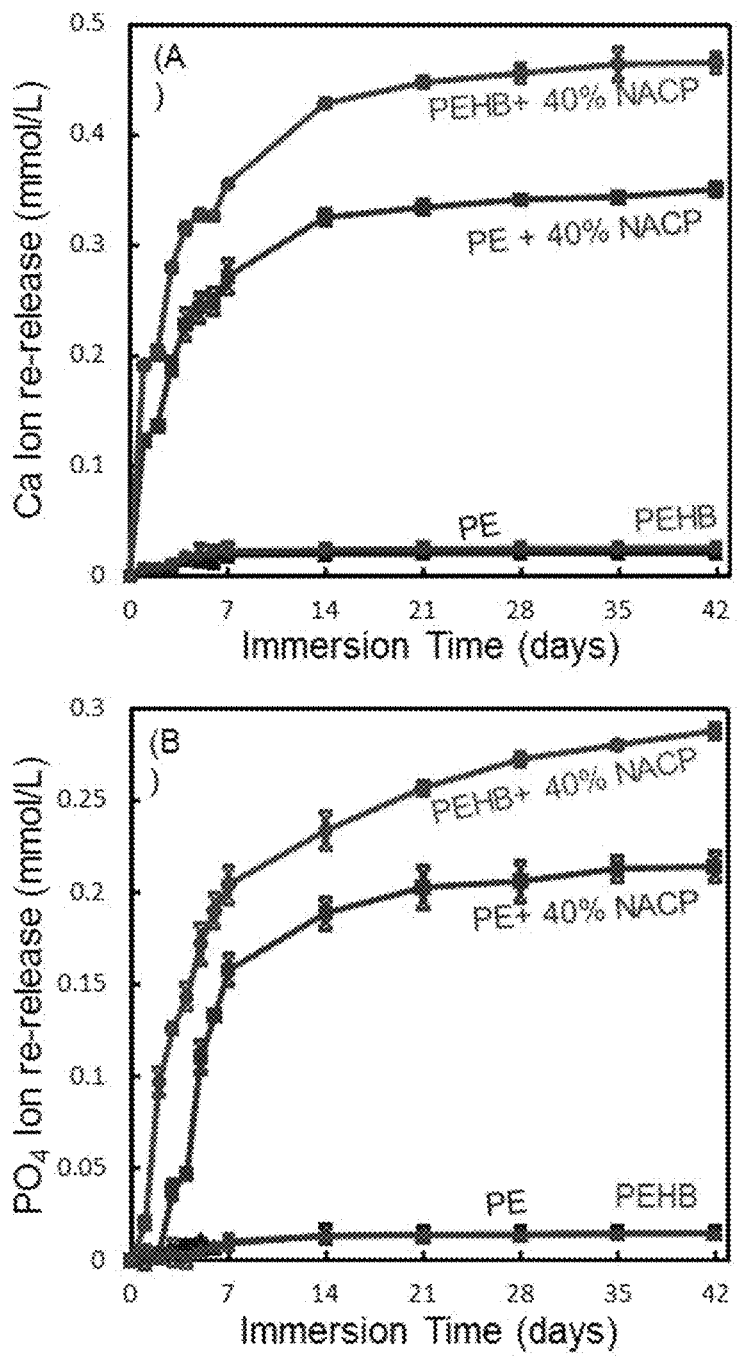
FIGS. 15A-15B. The continuous Ca (FIG. 15A) and P (FIG. 15B) re-release for 42 d after the third recharge (mean±sd; n=3). PEHB+40% NACP showed the significant higher Ca and $PO_4$ ion re-release than that of PE+40% NACP (p<0.05). The ion concentration increased for about 21 d and then gradually showed plateauing.

After the third recharge/re-release cycle, the continuous Ca and P ion re-release after the third recharge/re-release cycle (without further recharge) are plotted in FIG. 15. The measurement was continued for 42 d. Each value is mean±sd, with n=3. Cements PE and PEHB both showed little Ca (FIG. 15A) and P (FIG. 15B) ion re-release during the 42 d. PEHB+40% NACP showed higher Ca and P ion re-release than PE+40% NACP ($p<0.05$). The released ion concentrations significantly increased form 1 d to about 21 d and then gradually reached a plateau. These results demonstrate that cement PEHB+40% NACP and PE+40% NACP could release ions for around 21 d in a pH 4 immersion solution after recharge.

CaP orthodontic cements that are capable of releasing high level of Ca/P ion allow freely available calcium and phosphate ions to enter enamel and reform into crystals, which in turn help in preventing demineralization and enhancing remineralization [47,62]. In the present application, NACP orthodontic cements with capabilities of Ca/P ion release and recharge were developed for the first time. Among the four tested NACP cements, cement PEHB+40% NACP showed the highest Ca/P ion release and recharge capabilities, as well as a high bracket bonding property. This novel rechargeable CaP cement is especially advantageous in management of WSL because it can repeatedly be complemented with Ca/P ions using easy and friendly-handled recharging protocols and thus maintains a long-term lasting caries inhibition and enamel remineralization.

All documents, books, manuals, papers, patents, published patent applications, guides, abstracts and other reference materials cited herein are incorporated by reference in their entirety.

While the foregoing specification teaches the principles of the present invention, with examples provided for the purpose of illustration, it will be appreciated by one skilled in the art from reading this disclosure that various changes in form and detail can be made without departing from the true scope of the invention.

CITED DOCUMENTS

[1] Beazoglou T, Eklund S, Heffley D, Meiers J, Brown L J, Bailit H. Economic impact of regulating the use of amalgam restorations. Public Health Report 2007; 122: 657-663.

[2] Deligeorgi V, Mjor I A, Wilson N H. An overview of reasons for the placement and replacement of restorations. Primary Dental Care 2001; 8:5-11.

[3] Bohaty B S, Ye Q, Misra A, Sene F, Spencer P. Posterior composite restoration update: focus on factors influencing form and function. Clin Cosmet Investig Dent 2013; 15:33-42.

[4] Spencer P, Ye Q, Misra A, Goncalves S E, Laurence J S. Proteins, Pathogens, and Failure at the Composite-Tooth Interface. J Dent Res 2014; 93:1243-1249.

[5] Frost P M. An audit on the placement and replacement of restorations in a general dental practice. Prim Dent Care 2002; 9:31-36.

[6] National Institute of Dental and Craniofacial Research (NIDCR) announcement #13-DE-102, Dental Resin Composites and Caries, Mar. 5, 2009.

[7] Dickens S H, Flaim G M, Takagi S. Mechanical properties and biochemical activity of remineralizing resin-based Ca—PO4 cements. Dent Mater 2003; 19:558-66.

[8] Xu H H, Sun L, Weir M D, Antonucci J M, Takagi S, Chow L C, et al. Nano DCPA whisker composites with high strength and Ca and PO4 release. J Dent Res 2006; 85:722-7.

[9] Regnault W F, Icenogle T B, Antonucci J M, Skrtic D. Amorphous calcium phosphate/urethane methacrylate resin composites. I. Physicochemical characterization. J Mater Sci Mater Med 2008; 19:507-15.

[10] Langhorst S E, O'Donnell J N, Skrtic D. In vitro remineralization of enamel by polymeric amorphous calcium phosphate composite: quantitative microradiographic study. Dent Mater 2009; 25:884-91.

[11] Xu H H, Weir M D, Sun L, Moreau J L, Takagi S, Chow L C, et al. Strong nanocomposites with Ca, PO4, and F release for caries inhibition. J Dent Res 2010; 89:19-28.

[12] Katoh Y, Suzuki M, Kato C, Shinkai K, Ogawa M, Yamauchi J. Observation of calcium phosphate powder mixed with an adhesive monomer experimentally developed for direct pulp capping and as a bonding agent. Dent Mater J 2010; 29:15-24.

[13] Xu H H, Moreau J L, Sun L, Chow L C. Nanocomposite containing amorphous calcium phosphate nanoparticles for caries inhibition. Dent Mater 2011; 27:762-9.

[14] Liu Y, Tjäderhane L, Breschi L, Mazzoni A, Li N, Mao J, et al. Limitations in bonding to dentin and experimental strategies to prevent bond degradation. J Dent Res 2011; 90:953-68.

[15] Moreau J L, Sun L, Chow L C, Xu H H. Mechanical and acid neutralizing properties and bacteria inhibition of amorphous calcium phosphate dental nanocomposite. J Biomed Mater Res B Appl Biomater 2011; 98:80-8.

[16] Weir M D, Chow L C, Xu H H. Remineralization of demineralized enamel via calcium phosphate nanocomposite. J Dent Res 2012; 91:979-84.

[17] Melo M A, Weir M D, Rodrigues L K, Xu H H. Novel calcium phosphate nanocomposite with caries-inhibition in a human in situ model. Dent Mater 2013; 29:231-40.

[18] Xu H H, Weir M D, Sun L. Nanocomposites with Ca and PO4 release: effects of reinforcement, dicalcium phosphate particle size and silanization. Dent Mater 2007; 23:1482-1491.

[19] Chigira H, Koike T, Hasegawa T, Itoh K, Wakumoto S, Hayakawa T. Effect of the self etching dentin primers on the bonding efficacy of a dentin adhesive. Dent Mater J. 1989; 8(1):86-92.

[20] Cohen G S, Jia W. Dental self-etching composition comprising DOPA and method of use. U.S. Pat. Appl. Publ. (2006), US 20060084717 A1 Apr. 20, 2006.

[21] Hayakawa T, Kikutake K, Nemoto K. Efficacy of self-etching primers containing carboxylic acid monomers on the adhesion between composite resin and dentin. J Oral Science. 1998; 40:9-16.

[22] Moraes R R, Guimaraes G Z, Oliveira A S, Faot F, Cava S S. Impact of acidic monomer type and concentration on the adhesive performance of dental zirconia primers. Int J Adhesion and Adhesives. 2012; 39:49-53.

[23] Moszner N, Salz U, Zimmermann J. Chemical aspects of self-etching enamel-dentin adhesives: A systematic review. Dental Materials 2005; 21(10):895-910.

[24] Niihama M, Fukuda K, Une S. Photocurable dental adhesives containing acrylic monomers. Jpn. Kokai Tokkyo Koho (1993), JP 05286822A.

[25] Van Landuyt K L, Snauwaert J, De Munck J, Peumans M, Yoshida Y, Poitevin A, Coutinho E, Suzuki K, Lambrechts P, Van Meerbeek B. Systematic review of the chemical composition of contemporary dental adhesives. Biomaterials. 2007; 28(26):3757-3785.

[26] Venz S, Dickens B. Modified surface-active monomers for adhesive bonding to dentin J Dent Res 1993; 72(3): 582-586.

[27] Amirouche-Korichi A, Mouzali M, Watts D C. Effects of monomer ratios and highly radiopaque fillers on degree of conversion and shrinkage-strain of dentalresin composites. Dent Mater 2009; 25:1411-8.

[28] Meyer-Lueckel H, Hopfenmuller W, von Klinggraff D, Kielbassa A M. Microradiographic study on the effects of mucin-based solutions used as saliva substitutes on demineralised bovine enamel in vitro. Arch Oral Biol 2006; 51:541-7.

[29] Venz S, Dickens B. Modified Surface-active Monomers for Adhesive Bonding to Dentin. J Dent Res 1993; 72:582-586.

[30] Dickens S H, Kelly S R, Flaim G M, Giuseppetti A A. Dentin adhesion and microleakage of a resin-based calcium phosphate pulp capping and basing cement. Eur J Oral Sci 2004; 112:452-7.

[31] Featherstone J D B. The continuum of dental caries—Evidence for a dynamic disease process. J Dent Res 2004; 83:C39-C42.

[32] Thylstrup A, Fejerskov O. Textbook of cariology. Copenhagen, Denmark, Munksgaard, 1986, p. 145-146.

[33] Imazato S. Antibacterial properties of resin composites and dentin bonding systems. Dent Mater 2003; 19:449-57.

[34] Dickens S H, Flaim G M, Takagi S. Mechanical properties and biochemical activity of remineralizing resin-based Ca—PO4 cements. Dent Mater 2003; 19:558-66.

[35] Skrtic D, Antonucci J M, Liu D W. Ethoxylated bisphenol dimethacrylate-based amorphous calcium phosphate composites. Acta Biomater 2006; 2:85-94.

[36] Langhorst S E, O'Donnell J N, Skrtic D. In vitro remineralization of enamel by polymeric amorphous calcium phosphate composite: quantitative microradiographic study. Dent Mater 2009; 25:884-91.

[37] Melo M A, Cheng L, Weir M D, Hsia R C, Rodrigues L K, Xu H H. Novel dental adhesive containing antibacterial agents and calcium phosphate nanoparticles. J Biomed Mater Res B Appl Biomater 2013; 101:620-9.

[38] Chen C, Weir M D, Cheng L, Lin N J, Lin-Gibson S, Chow L C, et al. Antibacterial activity and ion release of bonding agent containing amorphous calcium phosphate nanoparticles. Dent Mater 2014; 30:891-901.

[39] Regnault W F, Icenogle T B, Antonucci J M, Skrtic D. Amorphous calcium phosphate/urethane methacrylate resin composites. I. Physicochemical characterization. J Mater Sci Mater Med 2008; 19:507-15.

[40] Xu X, Burgess J O. Compressive strength, fluoride release and recharge of fluoride-releasing materials. Biomaterials 2003; 24:2451-61.

[41] Xu H H, Moreau J L, Sun L, Chow L C. Nanocomposite containing amorphous calcium phosphate nanoparticles for caries inhibition. Dent Mater 2011; 27:762-9.

[42] Venz S, Dickens B. Modified surface-active monomers for adhesive bonding to dentin. J Dent Res 1993; 72:582-586.

[43] Milward P J, Adusei G O, Lynch C D. Improving some selected properties of dental polyacid-modified composite resins. Dent Mater 2011; 27:997-1002.

[44] Van Landuyt K L, Snauwaert J, De Munck J, Peumans M, Yoshida Y, Poitevin A, et al. Systematic review of the chemical composition of contemporary dental adhesives. Biomaterials 2007; 28:3757-85.

[45] Moreau J L, Sun L, Chow L C, Xu H H. Mechanical and acid neutralizing properties and bacteria inhibition of amorphous calcium phosphate dental nanocomposite. J Biomed Mater Res B Appl Biomater 2011; 98:80-8.

[46] Meyer-Lueckel H, Hopfenmuller W, von Klinggraff D, Kielbassa A M. Microradiographic study on the effects of mucin-based solutions used as saliva substitutes on demineralised bovine enamel in vitro. Arch Oral Biol 2006; 51:541-7.

[47] Reynolds E C, Cai F, Cochrane N J, Shen P, Walker G D, Morgan M V, Reynolds C: Fluoride and casein phosphopeptide-amorphous calcium phosphate. J Dent Res 2008; 87:344-348.

[48] Xu H H, Moreau J L, Sun L, Chow L C. Nanocomposite containing amorphous calcium phosphate nanoparticles for caries inhibition. Dent Mater 2011; 27:762-9.

[49] Weir M D, Chow L C, Xu H H. Remineralization of demineralized enamel via calcium phosphate nanocomposite. J Dent Res 2012; 91:979-84

[50] Melo M A, Weir M D, Rodrigues L K, Xu H H. Novel calcium phosphate nanocomposite with caries-inhibition in a human in situ model. Dent Mater 2013; 29:231-40.

[51] Chen C, Weir M D, Cheng L, Lin N J, Lin-Gibson S, Chow L C, Zhou X, Xu H H. Antibacterial activity and ion release of bonding agent containing amorphous calcium phosphate nanoparticles. Dent Mater 2014; 30:891-901.

[52] Moreau J L, Sun L, Chow L C, Xu H H. Mechanical and acid neutralizing properties and bacteria inhibition of amorphous calcium phosphate dental nanocomposite. J Biomed Mater Res B Appl Biomater 2011; 98:80-8.

[53] Dickens S H, Flaim G M, Takagi S. Mechanical properties and biochemical activity of remineralizing resin-based Ca—PO4 cements. Dent Mater 2003; 19:558-66.

[54] Regnault W F, Icenogle T B, Antonucci J M, Skrtic D. Amorphous calcium phosphate/urethane methacrylate resin composites. I. Physicochemical characterization. J Mater Sci Mater Med 2008; 19:507-15.

[55] Langhorst S E, O'Donnell J N, Skrtic D. In vitro remineralization of enamel by polymeric amorphous calcium phosphate composite: quantitative microradiographic study. Dent Mater 2009; 25:884-91.

[56] Van Landuyt K L, Snauwaert J, De Munck J, Peumans M, Yoshida Y, Poitevin A, Coutinho E, Suzuki K, Lambrechts P, Van Meerbeek B. Systematic review of the chemical composition of contemporary dental adhesives. Biomaterials 2007; 28:3757-85.

[57] Skrtic D, Antonucci J M, Liu D W. Ethoxylated bisphenol dimethacrylate-based amorphous calcium phosphate composites. Acta Biomater 2006; 2:85-94.

[58] Melo M A, Wu J, Weir M D, Xu H H. Novel antibacterial orthodontic cement containing quaternary ammonium monomer dimethylaminododecyl methacrylate. J Dent 2014; 42:1193-201.

[59] Skrtic D, Antonucci J M, Liu D W. Ethoxylated bisphenol dimethacrylate-based amorphous calcium phosphate composites. Acta Biomater 2006; 2:85-94.

[60] Xu H H, Sun L, Weir M D, Antonucci J M, Takagi S, Chow L C, Peltz M. Nano DCPA whisker composites with high strength and Ca and PO(4) release. J Dent Res 2006; 85:722-7.

[61] Meyer-Lueckel H, Hopfenmuller W, von Klinggraff D, Kielbassa A M. Microradiographic study on the effects of mucin-based solutions used as saliva substitutes on demineralised bovine enamel in vitro. Arch Oral Biol 2006; 51:541-7.

[62] Reynolds E C, Cai F, Shen P, Walker G D. Retention in plaque and remineralization of enamel lesions by various forms of calcium in a mouthrinse or sugar-free chewing gum. J Dent Res 2003; 82:206-11.

What is claimed is:

1. A rechargeable dental material comprising (i) a combination of rechargeable monomers and (ii) nanoparticles of amorphous calcium phosphate (NACP), wherein the combination of rechargeable monomers comprises about 10% to about 70% of the mass of the dental material, wherein the combination of rechargeable monomers comprises:

44.5% by mass pyromellitic glycerol dimethacrylate (PMGDM), 39.5% by mass ethoxylated bisphenol A dimethacrylate (EBPADMA), 10% by mass 2-hydroxyethyl methacrylate (HEMA), and 5% by mass bisphenol A glycidyl dimethacrylate (Bis-GMA);

wherein the NACP comprises about 30% of the mass of the dental material; and wherein the rechargeable dental material is a dental adhesive or a dental cement.

2. The rechargeable dental material according to claim 1, wherein the rechargeable dental material is a dental adhesive further comprising one or more curing agents, wherein the combined amount of the one or more curing agents is about 0.05% to about 5% of the mass of the rechargeable dental material.

3. The rechargeable material according to claim 1, wherein the rechargeable dental material is a dental cement further comprising one or more curing agents, wherein the combined amount of the one or more curing agents is about 0.05% to about 5% of the mass of the rechargeable dental material.

4. The rechargeable material according to claim 1, further comprising one or more fillers selected from the group consisting of glass fillers, ceramic fillers, and polymer fillers, wherein the combined amount of the one or more fillers is about 30% to about 70% of the mass of the rechargeable dental material.

5. The rechargeable dental material according to claim 1, further comprising one or more antibacterial agents selected from the group consisting of antibacterial monomers, quaternary ammonium salts (QASs), silver-containing nanoparticles (NanoAgs), chlorhexidine particles, TiO2 particles, and ZnO particles.

6. The rechargeable dental material according to claim 5, wherein the antibacterial monomers are selected from the group consisting of dimethylamino propyl methacrylate (DMAPM), dimethylamino hexyl methacrylate (DMAHM), dimethylamino heptyl methacrylate (DMAHPM), dimethylamino octyl methacrylate (DMAOM), dimethylamino nonyl methacrylate (DMANM), dimethylamino decyl methacrylate (DMADM), dimethylamino undecyl methacrylate (DMAUDM), dimethylamino dodecyl methacrylate (DMADDM), dimethylamino tridecyl methacrylate (DMATDM), dimethylamino tetradecyl methacrylate (DMATTDM), dimethylamino pentadecyl methacrylate (DMAPDM), dimethylamino hexadecyl methacrylate (DMAHDM), dimethylamino heptadecyl methacrylate (DMAHPDM), dimethylamino octadecyl methacrylate (DMAODM), dimethylamino nonadecyl methacrylate (DMANDM), dimethylamino icosyl methacrylate (DMAIOM), dimethylamino henicosyl methacrylate (DMAHOM), and dimethylamino docosyl methacrylate (DMADOM).

7. The rechargeable dental material according to claim 1, further comprising one or more protein repellant materials selected from the group consisting of 2-methacryloyloxyethyl phosphorylcholine (MPC), poly(hydroxyethyl methacrylate) (pHEMA) and derivatives thereof, and poly(N-isopropylacrylamide) and derivatives thereof.

8. The rechargeable dental material according to claim 2, wherein the one or more curing agents are selected from the group consisting of camphorquinone (CQ), benzoyl peroxide (BPO), phenylbis (2,4,6-triemthylbenzoyl) phosphine oxide, and ethyl 4-N,N-dimethylaminobenzoate.

9. The rechargeable dental material according to claim 1, wherein the NACP has an average particle size of about 10 nm to about 500 nm.

10. The rechargeable dental composite according to claim 4, wherein the glass filler is one or more glass particles selected from the group consisting of barium boroaluminosilicate glass particles, fluoroaluminosilicate glass particles modified with a polyalkenoic acid, and fluoroaluminosilicate glass particles modified with a polycarboxylic acid.

11. The rechargeable dental composite according to claim 4, wherein the filler is present in an amount of about 40% to about 60% by mass of the rechargeable dental material.

12. The dental adhesive of claim 2, wherein the dental adhesive further comprises phenylbis (2,4,6-trimethylbenzoyl) phosphine oxide (BAPO), wherein the amount of BAPO is about 1% of the mass of the rechargeable dental material.

13. The dental cement of claim 3, wherein the dental cement further comprises benzoyl peroxide (BPO) and camphorquinone (CQ), wherein the amount of BPO is about 0.8% of the mass of the rechargeable dental material and the amount of CQ is about 0.2% of the mass of the rechargeable dental material.

* * * * *